(12) United States Patent
Li et al.

(10) Patent No.: US 10,208,065 B2
(45) Date of Patent: Feb. 19, 2019

(54) CRYSTALLINE FREE BASES OF C-MET INHIBITOR OR CRYSTALLINE ACID SALTS THEREOF, AND PREPARATION METHODS AND USES THEREOF

(71) Applicant: Jiangsu Hansoh Pharmaceutical Group Co., Ltd., Lianyungang, Jiangsu (CN)

(72) Inventors: Xiang Li, Jiangsu (CN); Aifeng Lv, Jiangsu (CN)

(73) Assignee: JIANGSU HANSOH PHARMACEUTICAL GROUP CO., LTD., Lianyungang, Jiangsu (CN)

( * ) Notice: Subject to any disclaimer, the term of this patent is extended or adjusted under 35 U.S.C. 154(b) by 0 days.

(21) Appl. No.: 15/328,795

(22) PCT Filed: Jul. 30, 2015

(86) PCT No.: PCT/CN2015/085514
§ 371 (c)(1),
(2) Date: Jan. 24, 2017

(87) PCT Pub. No.: WO2016/015653
PCT Pub. Date: Feb. 4, 2016

(65) Prior Publication Data
US 2017/0210760 A1    Jul. 27, 2017

(30) Foreign Application Priority Data

Aug. 1, 2014    (CN) .......................... 2014 1 0378371

(51) Int. Cl.
*C07D 519/00*    (2006.01)
*A61K 31/5383*    (2006.01)

(52) U.S. Cl.
CPC ........ *C07D 519/00* (2013.01); *A61K 31/5383* (2013.01); *C07B 2200/13* (2013.01)

(58) Field of Classification Search
CPC .............. C07D 519/00; C07B 2200/13; A61K 31/5383

USPC .......................................................... 546/83
See application file for complete search history.

(56) References Cited

U.S. PATENT DOCUMENTS 9,512,121 B2 * 12/2016  Zhao .................... C07D 519/00

FOREIGN PATENT DOCUMENTS

| WO | 2013038362 A1 | 3/2013 |
| WO | 2014180182 | * 11/2014 |
| WO | 2014180182 A1 | 11/2014 |

OTHER PUBLICATIONS

Lian Yu, 2001, Amorphous Pharmaceutical Solids.*
ICH Harmonised Tripartite Guideline (Year: 1999).*
Benedetta Peruzzi et al, Targeting the c-Met Signaling Pathway in Cancer (Year: 2006).*
Int'l Search Report dated Oct. 8, 2015 in Int'l Application No. PCT/CN2015/085514.

* cited by examiner

*Primary Examiner* — Rita J Desai
(74) *Attorney, Agent, or Firm* — Panitch Schwarze Belisario & Nadel LLP

(57) ABSTRACT

Crystalline free bases and crystalline acid salts of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one are disclosed as C-Met inhibitors. Their preparation methods and uses are also described. In particular, crystal forms I, II, III and IV of the free base; crystal form I of the hydrochloride salt; crystal forms I and II of the sulfate salt; crystal forms I, II, III and IV of the phosphate salt; crystal forms I, II, III, IV and V of the mesylate salt; crystal forms I, II and III of the p-toluenesulfonate salt; and crystal forms I, II and III of the 1,5-naphthalenedisulfonate salt are disclosed. Also disclosed are methods for preparing the above-mentioned crystal forms, pharmaceutical compositions thereof, methods for regulating the catalytic activity of a protein kinase, and methods of treating protein kinase-related diseases.

19 Claims, 14 Drawing Sheets

CRYSTALLINE FREE BASES OF C-MET INHIBITOR OR CRYSTALLINE ACID SALTS THEREOF, AND PREPARATION METHODS AND USES THEREOF

CROSS-REFERENCE TO RELATED APPLICATION

This application is a Section 371 of International Application No. PCT/CN2015/085514, filed Jul. 30, 2015, which was published in the Chinese language on Feb. 4, 2016, under International Publication No. WO 2016/015653 A1, and the disclosure of which is incorporated herein by reference.

FIELD OF THE INVENTION

The present invention relates to the field of drugs, and specifically relates to crystalline free bases of c-met inhibitor or crystalline acid salts thereof, and preparation methods and uses thereof.

BACKGROUND OF THE INVENTION

Hepatocyte growth factor (HGF) receptor, also known as C-Met, is a tyrosine kinase receptor. Abnormal activation of C-Met is related to a poor prognosis of cancer, when there is a problem of C-Met overexpression. C-Met abnormality is also found in many types of tumors, such as hepatocellular carcinoma (HCC), non-small cell lung cancer (NSCLC), bladder cancer, liver cancer, kidney cancer, stomach cancer, breast cancer, squamous cell carcinoma, brain cancer, colon cancer, etc. C-Met abnormality can be expressed as increased expression, gene amplification, gene mutation or increased expression of HGF. In these abnormal circumstances, C-Met is activated in an abnormal state, which results in carcinogenesis and poor prognosis. Abnormal activation of C-Met will lead to tumor growth, formation of new blood vessels (angiogenesis, which can provide nutrients to the tumor), and help the cancer spread to other organs (metastasis). Inhibition of the C-Met signaling pathway is thus an important therapeutic strategy for the treatment of cancer.

C-Met inhibitors having pharmacological activity are described by Jiangsu Hansoh Company in the Chinese patent application CN201310173581.4 and the PCT application thereof (PCT/CN2014/072825). One of the compounds described is 9-((8-fluoro-6-(1-methyl-1H-pyrazol-4-yl)-[1,2,4]triazolo[4,3-a]pyridine-3-yl)thio)-4-m ethyl-2H-[1,4]oxaazido[3,2-c]quinoline-3(4H)-one (referred to as "compound of formula I").

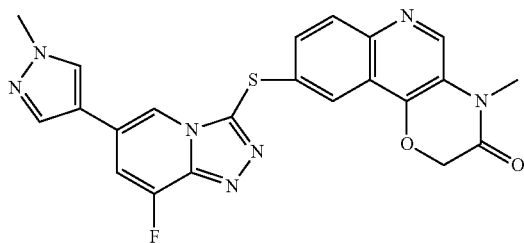

Compound of formula I

The compound of formula I is a valid C-Met/HGFR (hepatocyte growth factor receptor) kinase inhibitor. As a C-Met tyrosine kinase inhibitor, the compound of formula I can effectively block the HGF/C-Met signal transduction pathway for the purpose of treating abnormal cell growth (e.g. cancer) in mammals. However, in the patent application CN201310173581.4 and the PCT application thereof (PCT/CN2014/72825), only an amorphous form of the compound of formula I was described. It is well known that the amorphous form of a drug means that the drug molecules aggregate in a disorderly manner, and the drug does not contain a significant lattice. The amorphous form of the drug has a higher thermodynamic energy state than the crystalline form, which results in thermodynamic instability. Thermodynamic instability leads to poor chemical stability, easy moisture absorption and solid phase transition. Accordingly, the quality of the drug is extremely unstable. Therefore, it is difficult for the amorphous form to be used in drug development. Furthermore, during drug preparation, the process of drug crystallization is an effective purification method. The resulting crystalline form also has the technological operation advantage of easy further purification, easy filtration, drying and so on. Therefore, it is necessary to further research and develop new crystal forms which have good crystallinity, moderate size, good solubility, and high stability in order to improve the bioavailability of the drug. The patent application CN201310173581.4 and the PCT application thereof (PCT/CN2014/072825) disclosed an amorphous free base of the compound of formula I. Said free base has a low solubility in various solvents, which is not conducive to drug dissolution in an animal or human body. Therefore, it is a very urgent task to research and develop suitable salt-form compounds in order to improve the dissolution rate and the solubility of the compound of formula I.

In summary, for the amorphous free base, further technical improvements are needed in drug purification, drying, storage, formulation, and dissolution and so on, in order to improve drug bioavailability.

DESCRIPTION OF THE INVENTION

In order to solve the technical problems in the prior art, the present invention provides a crystalline free base or a crystalline acid salt of 9-((8-fluoro-6-(1-methyl-1H-pyrazol-4-yl)-[1,2,4]triazolo[4,3-a]pyridine-3-yl)thio)-4-m ethyl-2H-[1,4]oxaazido[3,2-c]quinoline-3(4H)-one (i.e., the compound of formula I), a preparation method thereof and medical uses thereof. The physical and chemical properties of the compound of formula I, such as solubility, hygroscopicity and chemical stability have been greatly improved by intensive study of the different aggregation states.

In one aspect, the invention provides a crystalline free base of 9((8-fluoro-6-(1-methyl-1H-pyrazol)-4-yl)-[1,2,4] triazolo[4,3-a]pyridine-3-yl)thio)-4-m ethyl-2H-[1,4]oxaazido[3,2-c]quinoline-3(4H)-one (i.e., the compound of formula I). The polymorphs of the free base include four crystal forms, referred to as crystal form I, crystal form II, crystal form III and crystal form IV, respectively.

The invention provides a crystal form I of the free base of the compound of formula I having an X-ray powder diffraction spectrum comprising peaks at diffraction angles (2θ) of 13.0±0.2°, 17.9±0.2°, 21.2±0.2° and 31.4±0.2°.

Preferably, the X-ray powder diffraction spectrum further comprises peaks at diffraction angles (2θ) of 10.3±0.2°, 11.1±0.2°, 23.3±0.2°, 23.8±0.2° and 33.6±0.2°.

More preferably, the X-ray powder diffraction spectrum further comprises peaks at diffraction angles (2θ) of 15.7±0.2°, 17.7±0.2°, 26.8±0.2°, 28.0±0.2°, 31.7±0.2° and 32.8±0.2°.

Most preferably, the X-ray powder diffraction spectrum comprises substantially the same peaks at diffraction angles (2θ) as shown in FIG. 1, and the X-ray powder diffraction data are shown in Table 1:

TABLE 1

| 2θ (°) | intensity % |
|---|---|
| 5.3 | 4.5 |
| 10.3 | 24.9 |
| 10.5 | 11.9 |
| 11.1 | 28.5 |
| 12.7 | 9.9 |
| 13.0 | 36.3 |
| 13.9 | 5.6 |
| 14.7 | 7.0 |
| 15.1 | 4.4 |
| 15.4 | 7.4 |
| 15.7 | 13.8 |
| 17.7 | 15.0 |
| 17.9 | 47.6 |
| 19.4 | 8.7 |
| 20.3 | 7.5 |
| 20.6 | 2.8 |
| 21.2 | 100.0 |
| 22.8 | 4.1 |
| 23.3 | 27.3 |
| 23.8 | 27.2 |
| 25.9 | 3.2 |
| 26.6 | 5.9 |
| 26.8 | 19.0 |
| 27.1 | 6.8 |
| 27.3 | 5.8 |
| 28.0 | 13.8 |
| 31.4 | 33.4 |
| 31.7 | 18.4 |
| 32.8 | 12.3 |
| 33.6 | 21.1 |
| 35.8 | 6.3 |
| 38.1 | 6.8 |
| 38.8 | 10.3 |

The invention provides a crystal form II of the free base of the compound of formula I having an X-ray powder diffraction spectrum comprising peaks at diffraction angles (2θ) of 8.6±0.2°, 11.5±0.2°, 14.1±0.2° and 19.8±0.2°.

Preferably, the X-ray powder diffraction spectrum further comprises peaks at diffraction angles (2θ) of 11.9±0.2°, 14.7±0.2°, 15.2±0.2°, 17.2±0.2° and 18.9±0.2°.

More preferably, the X-ray powder diffraction spectrum further comprises peaks at diffraction angles (2θ) of 5.8±0.2°, 7.4±0.2°, 20.9±0.2°, 30.9±0.2°, 31.4±0.2° and 37.9±0.2°.

Most preferably, the X-ray powder diffraction spectrum comprises substantially the same peaks at diffraction angles (2θ) as shown in FIG. 4, and the X-ray powder diffraction data are shown in Table 2:

TABLE 2

| 2θ (°) | intensity % |
|---|---|
| 5.8 | 2.1 |
| 7.4 | 2.8 |
| 8.6 | 100.0 |
| 11.5 | 13.3 |
| 11.9 | 5.6 |
| 14.1 | 10.5 |
| 14.7 | 6.2 |
| 15.2 | 4.7 |

TABLE 2-continued

| 2θ (°) | intensity % |
|---|---|
| 17.2 | 7.8 |
| 18.9 | 5.1 |
| 19.8 | 9.6 |
| 20.9 | 2.0 |
| 30.9 | 3.5 |
| 31.4 | 4.0 |
| 37.9 | 2.2 |

The invention provides crystal form III of free base of the compound of formula I having an X-ray powder diffract km spectrum comprising peaks at diffraction angles (2θ) of 12.8±0.2°, 14.8±0.2°, 18.0±0.2° and 20.5±0.2°.

Preferably, the X-ray powder diffraction spectrum further comprises peaks at diffraction angles (2θ) of 8.9±0.2°, 9.2±0.2°, 10.6±0.2°, 15.8±0.2° and 20.7±0.2°.

More preferably, the X-ray powder diffraction spectrum further comprises peaks at diffraction angles (2θ) of 5.3±0.2°, 5.9±0.2°, 12.0±0.2°, 14.0±0.2°, 17.3±0.2° and 19.9±0.2°.

Most preferably, the X-ray powder diffraction spectrum comprises substantially the same peaks at diffraction angles (2θ) as shown in FIG. 5, and the X-ray powder diffraction data are shown in Table 3:

TABLE 3

| 2θ (°) | intensity % |
|---|---|
| 5.3 | 8.2 |
| 5.9 | 11.7 |
| 7.9 | 7.6 |
| 8.9 | 18.9 |
| 9.2 | 19.1 |
| 10.6 | 14.8 |
| 12.0 | 12.8 |
| 12.8 | 30.4 |
| 13.3 | 6.6 |
| 14.0 | 8.6 |
| 14.8 | 31.3 |
| 15.8 | 26.2 |
| 17.3 | 10.4 |
| 18.0 | 100.0 |
| 19.9 | 11.4 |
| 20.5 | 32.8 |
| 20.7 | 24.9 |

The invention provides a crystal form IV of the free base of the compound of formula I having an X-ray powder diffraction spectrum comprising peaks at diffraction angles (2θ) of 8.9±0.2°, 12.6±0.2°, 17.0±0.2° and 17.9±0.2°.

Preferably, the X-ray powder diffraction spectrum further comprises peaks at diffraction angles (2θ) of 13.2±0.2°, 14.5±0.2°, 20.5±0.2°, 23.9±0.2° and 26.3±0.2°.

Most preferably, the X-ray powder diffraction spectrum comprises substantially the same peaks at diffraction angles (2θ) as shown in FIG. 7, and the X-ray powder diffraction data are shown in Table 4:

TABLE 4

| 2θ (°) | intensity % |
|---|---|
| 8.9 | 100.0 |
| 12.6 | 34.5 |
| 13.2 | 14.6 |
| 14.5 | 13.8 |
| 17.0 | 16.1 |
| 17.9 | 15.1 |
| 20.5 | 11.1 |

TABLE 4-continued

| 2θ (°) | intensity % |
|---|---|
| 23.9 | 6.7 |
| 26.3 | 13.9 |
| 29.0 | 6.5 |

In another aspect, the invention provides a crystalline acid salt of 9-((8-fluoro-6-(1-methyl-1H-pyrazol-4-yl)-[1,2,4]triazolo[4,3-a]pyridine-3-yl)thio)-4-m ethyl-2H-[1,4]oxaazido[3,2-c]quinoline-3(4H)-one.

The acid salt comprises an inorganic acid salt and an organic acid salt. The inorganic acid salt is preferably selected from the group consisting of hydrochloride, sulfate, hydrobromide, hydrofluoride, hydroiodide and phosphate, and is more preferably selected from the group consisting of hydrochloride, sulfate and phosphate. The organic acid salt is preferably selected from the group consisting of 2,5-dihydroxybenzeneformate, 1-hydroxy-2-naphthaleneformate, acetate, dichloroacetate, trichloroacetate, acetohydroxamate, adipate, benzene sulfonate, 4-chlorobenzene sulfonate, benzeneformate, 4-acetamidobenzeneformate, 4-aminobenzeneformate, caprate, caproate, caprilate, cinnamoate, citrate, cyclohexylsulfamate, camphorsulfonate, aspartate, camphorate, gluconate, glucuronate, glutamate, erythorbate, lactate, aspartate, malate, mandelate, pyroglutamate, tartrate, lauryl sulfate dibenzoyltartrate, ethyl-1,2-disulfonate, esylate, formate, fumarate, galactonate, gentisate, glutarate, 2-oxoglutarate, glycollate, hippurate, isethionate, lactobionate, ascorbate, aspartate, laurate, camphorate, maleate, malonate, mesylate, 1,5-naphthalenedisulfonate, naphthalene-2-sulfonate, nicotinate, oleate, orotate, oxalate, palmitate, embonate, propionate, salicylate, 4-aminosalicylate, sebacate, stearate, butanedioate, thiocyanate, undecylenate, trifluoroacetate, succinate and p-toluenesulfonate, and is more preferably selected from the group consisting of mesylate, p-toluenesulfonate and 1,5-naphthalenedisulfonate.

The invention provides a polymorph of a hydrochloride of the compound of formula I, comprising one crystal form, referred to as crystal form I, which has an X-ray powder diffraction spectrum comprising peaks at diffraction angles (2θ) of 8.1±0.2°, 19.2±0.2°, 24.1±0.2° and 26.2±0.2°.

Preferably, the X-ray powder diffraction spectrum further comprises peaks at diffraction angles (2θ) of 9.1±0.2°, 11.3±0.2°, 13.4±0.2°, 29.7±0.2° and 23.4±0.2°.

More preferably, the X-ray powder diffraction spectrum comprises substantially the same peaks at diffraction angles (2θ) as shown in FIG. 8, and the X-ray powder diffraction data are shown in Table 5:

TABLE 5

| 2θ (°) | intensity % |
|---|---|
| 6.7 | 8.1 |
| 8.1 | 100.0 |
| 9.1 | 8.8 |
| 11.3 | 16.6 |
| 13.4 | 12.6 |
| 19.2 | 39.0 |
| 23.4 | 10.6 |
| 24.1 | 21.4 |
| 26.2 | 41.4 |
| 29.7 | 14.0 |
| 30.8 | 5.6 |
| 33.5 | 6.3 |

The invention provides a polymorph of a sulfate of the compound of formula I, comprising two crystal forms, referred to as crystal form I and crystal form II, respectively.

The invention provides a crystal form I of a sulfate of the compound of formula I having an X-ray powder diffraction spectrum comprising peaks at diffraction angles (2θ) of 18.4±0.2°, 19.7±0.2°, 23.8±0.2° and 24.5±0.2°.

Preferably, the X-ray powder diffraction spectrum further comprises peaks at diffraction angles (2θ) of 12.8±0.2°, 14.4±0.2°, 17.0±0.2°, 20.0±0.2° and 21.0±0.2°.

More preferably, the X-ray powder diffraction spectrum further comprises peaks at diffraction angles (2θ) of 8.7±0.2°, 13.2±0.2°, 19.1±0.2°, 26.3±0.2°, 26.6±0.2° and 29.0±0.2°.

Most preferably, the X-ray powder diffraction spectrum comprises substantially the same peaks at diffraction angles (2θ) as shown in FIG. 9, and the X-ray powder diffraction data are shown in Table 6:

TABLE 6

| 2θ (°) | intensity % |
|---|---|
| 5.7 | 19.7 |
| 6.6 | 14.9 |
| 8.7 | 37.2 |
| 9.9 | 13.6 |
| 11.0 | 33.6 |
| 12.8 | 45.8 |
| 13.2 | 40.1 |
| 14.4 | 78.3 |
| 17.0 | 75.6 |
| 17.4 | 27.5 |
| 18.4 | 100.0 |
| 19.1 | 38.8 |
| 19.7 | 84.5 |
| 20.0 | 49.4 |
| 21.0 | 58.7 |
| 21.6 | 32.0 |
| 22.7 | 25.3 |
| 23.8 | 89.8 |
| 24.5 | 83.2 |
| 24.9 | 28.3 |
| 26.3 | 45.2 |
| 26.6 | 41.1 |
| 29.0 | 41.6 |

The invention provides a crystal form II of a sulfate of the compound of formula I having an X-ray powder diffraction spectrum comprising peaks at diffraction angles (2θ) of 6.3±0.2°, 8.7±0.2°, 12.7±0.2° and 18.4±0.2°.

Preferably, the X-ray powder diffraction spectrum further comprises peaks at diffraction angles (2θ) of 8.3±0.2°, 17.5±0.2°, 18.7±0.2°, 20.4±0.2° and 25.6±0.2°.

More preferably, the X-ray powder diffraction spectrum further comprises peaks at diffraction angles (2θ) of 9.1±0.2°, 15.9±0.2°, 16.8±0.2°, 24.0±0.2°, 25.2±0.2° and 28.4±0.2°.

Most preferably, the X-ray powder diffraction spectrum comprises substantially the same peaks at diffraction angles (2θ) as shown in FIG. 10, and, the X-ray powder diffraction data are shown in Table 7:

TABLE 7

| 2θ (°) | intensity % |
|---|---|
| 6.3 | 84.8 |
| 8.3 | 26.9 |
| 8.7 | 100.0 |
| 9.1 | 11.6 |
| 9.5 | 6.4 |

TABLE 7-continued

| 2θ (°) | intensity % |
|---|---|
| 12.7 | 53.8 |
| 15.9 | 11.7 |
| 16.8 | 11.0 |
| 17.5 | 46.7 |
| 18.4 | 49.8 |
| 18.7 | 22.9 |
| 20.4 | 21.6 |
| 24.0 | 13.4 |
| 24.6 | 5.9 |
| 25.2 | 18.0 |
| 25.6 | 26.7 |
| 28.4 | 14.8 |

The invention provides a polymorph of a Phosphate of the compound of formula I, comprising four crystal forms, referred to as crystal form I, crystal form II, crystal form III and crystal form IV, respectively.

The invention provides a crystal form I of a phosphate of the compound of formula I having an X-ray powder diffraction spectrum comprising peaks at diffraction angles (2θ) of 7.9±0.2°, 12.8±0.2°, 15.9±0.2° and 18.3±0.2°.

Preferably, the X-ray powder diffraction spectrum further comprises peaks at diffraction angles (2θ) of 5.3±0.2°, 10.6±0.2°, 13.4±0.2°, 20.9±0.2° and 24.7±0.2°.

More preferably, the X-ray powder diffraction spectrum further comprises peaks at diffraction angles (2θ) of 16.5±0.2°, 18.7±0.2°, 20.6±0.2°, 21.8±0.2°, 26.2±0.2° and 27.4±0.2°.

Most preferably, the X-ray powder diffraction spectrum comprises substantially the same peaks at diffraction angles (2θ) as shown in FIG. 11, and the X-ray powder diffraction data are shown in Table 8:

TABLE 8

| 2θ (°) | intensity % |
|---|---|
| 5.3 | 18.2 |
| 7.9 | 100.0 |
| 10.6 | 15.6 |
| 12.8 | 26.2 |
| 13.4 | 11.5 |
| 15.9 | 27.5 |
| 16.5 | 6.3 |
| 17.3 | 4.2 |
| 18.3 | 62.0 |
| 18.7 | 9.4 |
| 19.3 | 3.4 |
| 20.6 | 4.6 |
| 20.9 | 10.5 |
| 21.8 | 6.0 |
| 23.1 | 3.5 |
| 24.7 | 16.5 |
| 25.1 | 4.0 |
| 26.2 | 4.6 |
| 27.4 | 9.5 |

The invention provides a crystal form II of a phosphate of the compound of formula I having an X-ray powder diffraction spectrum comprising peaks at diffraction angles (2θ) of 13.7±0.2°, 16.1±0.2°, 22.8±0.2° and 26.1±0.2°.

Preferably, the X-ray powder diffraction spectrum further comprises peaks at diffraction angles (2θ) of 11.0±0.2°, 14.6±0.2°, 20.3±0.2°, 20.8±0.2° and 25.7±0.2°.

More preferably, the X-ray powder diffraction spectrum further comprises peaks at diffraction angles (2θ) of 6.8±0.2°, 17.0±0.2°, 22.2±0.2°, 26.6±0.2°, 27.9±0.2° and 31.2±0.2°.

Most preferably, the X-ray powder diffraction spectrum comprises substantially the same peaks at diffraction angles (2θ) as shown in FIG. 12, and the X-ray powder diffraction data are shown in Table 9:

TABLE 9

| 2θ (°) | intensity % |
|---|---|
| 6.8 | 26.3 |
| 8.8 | 6.1 |
| 11.0 | 71.5 |
| 12.4 | 12.9 |
| 13.7 | 87.5 |
| 14.6 | 30.8 |
| 16.1 | 74.6 |
| 17.0 | 30.3 |
| 20.3 | 32.2 |
| 20.8 | 34.1 |
| 21.5 | 11.6 |
| 22.2 | 20.1 |
| 22.8 | 100.0 |
| 24.6 | 16.3 |
| 25.7 | 47.1 |
| 26.1 | 94.2 |
| 26.6 | 30.0 |
| 27.9 | 26.4 |
| 30.7 | 14.1 |
| 31.2 | 21.7 |

The invention provides a crystal form II of a phosphate of the compound of formula I having an X-ray powder diffraction spectrum comprising peaks at diffraction angles (2θ) of 9.7±0.2°, 15.6±0.2°, 16.8±0.2° and 24.6±0.2°.

Preferably, the X-ray powder diffraction spectrum further comprises peaks at diffraction angles (2θ) of 4.8±0.2°, 21.2±0.2°, 25.0±0.2°, 27.8±0.2° and 28.1±0.2°.

More preferably, the X-ray powder diffraction spectrum further comprises peaks at diffraction angles (2θ) of 5.2±0.2°, 12.8±0.2°, 14.5±0.2°, 18.0±0.2°, 20.1±0.2 and 23.5±0.2°.

Most preferably, the X-ray powder diffraction spectrum comprises substantially the same peaks at diffraction angles (2θ) as shown in FIG. 13, and, the X-ray powder diffraction data are shown in Table 10:

TABLE 10

| 2θ (°) | intensity % |
|---|---|
| 4.8 | 26.0 |
| 5.2 | 20.8 |
| 7.8 | 5.2 |
| 9.7 | 49.4 |
| 10.7 | 6.1 |
| 12.4 | 10.1 |
| 12.8 | 21.4 |
| 14.5 | 14.7 |
| 15.6 | 41.0 |
| 16.8 | 100.0 |
| 18.0 | 21.0 |
| 19.2 | 11.7 |
| 20.1 | 16.5 |
| 21.2 | 36.9 |
| 22.6 | 12.2 |
| 23.5 | 12.5 |
| 24.6 | 86.0 |
| 25.0 | 39.2 |
| 26.8 | 11.3 |
| 27.8 | 29.3 |
| 28.1 | 24.0 |

The invention provides a crystal form IV of a phosphate of the compound of formula I having an X-ray powder diffraction spectrum comprising peaks at diffraction angles (2θ) of 7.8±0.2°, 17.9±0.2°, 25.0±0.2° and 27.7±0.2°.

Preferably, the X-ray powder diffraction spectrum further comprises peaks at diffraction angles (2θ) of 6.7±0.2°, 10.8±0.2°, 15.6±0.2°, 23.4±0.2° and 24.6±0.2°.

More preferably, the X-ray powder diffraction spectrum further comprises peaks at diffraction angles (2θ) of 5.2±0.2°, 12.8±0.2°, 20.9±0.2°, 21.7±0.2°, 22.3±0.2° and 26.8±0.2°.

Most preferably, the X-ray powder diffraction spectrum comprises substantially the same peaks at diffraction angles (2θ) as shown in FIG. 14, and the X-ray powder diffraction data are shown in Table 11:

TABLE 11

| 2θ (°) | intensity % |
|---|---|
| 5.2 | 13.9 |
| 6.7 | 24.2 |
| 7.8 | 76.3 |
| 10.8 | 31.8 |
| 12.4 | 5.6 |
| 12.8 | 17.4 |
| 13.3 | 6.3 |
| 15.6 | 36.9 |
| 17.9 | 100.0 |
| 19.6 | 5.1 |
| 20.9 | 10.8 |
| 21.7 | 10.5 |
| 22.3 | 7.8 |
| 23.4 | 25.6 |
| 24.6 | 47.5 |
| 25.0 | 84.6 |
| 26.8 | 7.7 |
| 27.7 | 70.6 |

The invention provides a polymorph of a mesylate of the compound of formula I, comprising five crystal forms, referred to as crystal form I, crystal form II, crystal form III, crystal form IV and crystal form V, respectively.

The invention provides a crystal form I of a mesylate of the compound of formula I having an X-ray powder diffraction spectrum comprising peaks at diffraction angles (2θ) of 15.6±0.2°, 17.0±0.2°, 25.6±0.2° and 26.0±0.2°.

Preferably, the X-ray powder diffraction spectrum further comprises peaks at diffraction angles (2θ) of 9.8±0.2°, 21.8±0.2°, 23.5±0.2°, 23.8±0.2° and 27.5±0.2°.

More preferably, the X-ray powder diffraction spectrum further comprises peaks at diffraction angles (2θ) of 6.6±0.2°, 15.3±0.2°, 17.2±0.2°, 18.3±0.2°, 19.7±0.2° and 26.4±0.2°.

Most preferably, the X-ray powder diffraction spectrum comprises substantially the same peaks at diffraction angles (2θ) as shown in FIG. 15, and the X-ray powder is diffraction data are shown in Table 12:

TABLE 12

| 2θ (°) | intensity % |
|---|---|
| 6.6 | 27.5 |
| 9.8 | 46.7 |
| 10.9 | 13.5 |
| 13.1 | 5.6 |
| 15.3 | 15.2 |
| 15.6 | 71.4 |
| 16.2 | 5.8 |
| 17.0 | 66.8 |
| 17.2 | 21.7 |
| 18.3 | 17.9 |
| 19.7 | 18.9 |
| 20.1 | 7.7 |
| 20.5 | 14.5 |
| 21.5 | 6.3 |

TABLE 12-continued

| 2θ (°) | intensity % |
|---|---|
| 21.8 | 29.8 |
| 23.5 | 32.6 |
| 23.8 | 53.6 |
| 25.6 | 58.2 |
| 26.0 | 100.0 |
| 26.4 | 15.8 |
| 27.5 | 34.0 |
| 28.9 | 9.5 |
| 29.3 | 10.8 |
| 30.5 | 11.7 |
| 31.0 | 10.2 |
| 31.6 | 7.3 |
| 32.5 | 11.2 |
| 33.1 | 6.5 |
| 34.0 | 10.0 |

The invention provides a crystal form II of a mesylate of the compound of formula I having an X-ray powder diffraction spectrum comprising peaks at diffraction angles (2θ) of 9.4±0.2°, 17.0±0.2°, 18.9±0.2° and 27.3±0.2°.

Preferably, the X-ray powder diffraction spectrum further comprises peaks at diffraction angles (2θ) of 6.6±0.2°, 14.9±0.2°, 21.1±0.2°, 26.1±0.2° and 26.9±0.2°.

More preferably; the X-ray powder diffraction spectrum comprises substantially the same peaks at diffraction angles (2θ) as shown in FIG. 16, and the X-ray powder diffraction data are shown in Table 13:

TABLE 13

| 2θ (°) | intensity % |
|---|---|
| 6.6 | 33.4 |
| 9.4 | 66.5 |
| 14.9 | 42.7 |
| 17.0 | 100.0 |
| 18.9 | 61.2 |
| 19.5 | 20.1 |
| 21.1 | 22.5 |
| 23.7 | 19.8 |
| 26.1 | 46.3 |
| 26.9 | 34.7 |
| 27.3 | 61.6 |
| 36.1 | 15.3 |

The invention provides a crystal form III of a mesylate of the compound of formula I having an X-ray powder diffraction spectrum comprising peaks at diffraction angles (2θ) of 16.7±0.2°, 19.3±0.2°, 23.2±0.2° and 26.5±0.2°.

Preferably, the X-ray powder diffraction spectrum further comprises peaks at diffraction angles (2θ) of 8.7±0.2°, 19.5±0.2°, 21.8±0.2°, 23.6±0.2° and 24.3±0.2°.

More preferably, the X-ray powder diffraction spectrum further comprises peaks at diffraction angles (2θ) of 11.7±0.2°, 13.6±0.2°, 14.1±0.2°, 17.2±0.2°, 18.7±0.2° and 27.2±0.2°.

Most preferably, the X-ray powder diffraction spectrum comprises substantially the same peaks at diffraction angles (2θ) as shown in FIG. 17, and the X-ray powder diffraction data are shown in Table 14:

TABLE 14

| 2θ (°) | intensity % |
|---|---|
| 6.3 | 12.5 |
| 8.7 | 71.0 |
| 9.7 | 17.0 |
| 11.7 | 20.7 |

TABLE 14-continued

| 2θ (°) | intensity % |
|---|---|
| 12.0 | 20.6 |
| 12.5 | 5.4 |
| 13.6 | 28.1 |
| 14.1 | 23.9 |
| 16.7 | 100.0 |
| 17.2 | 40.2 |
| 17.9 | 13.0 |
| 18.7 | 21.6 |
| 19.3 | 74.2 |
| 19.5 | 53.0 |
| 20.2 | 7.6 |
| 21.8 | 50.8 |
| 22.3 | 10.6 |
| 23.2 | 72.7 |
| 23.6 | 56.4 |
| 24.3 | 58.6 |
| 24.8 | 12.3 |
| 25.2 | 7.1 |
| 26.5 | 80.7 |
| 27.2 | 40.6 |
| 28.5 | 6.8 |
| 30.8 | 15.4 |
| 31.1 | 15.4 |
| 33.4 | 14.1 |
| 36.8 | 7.0 |
| 37.5 | 14.4 |

The invention provides a crystal form IV of a mesylate of the compound of formula I having an X-ray powder diffraction spectrum comprising peaks at diffraction angles (2θ) of 16.8±0.2°, 19.1±0.2°, 19.3±0.2° and 22.1±0.2°.

Preferably, the X-ray powder diffraction spectrum further comprises peaks at diffraction angles (2θ) of 21.9±0.2°, 23.2±0.2°, 24.4±0.2°, 26.0±0.2° and 27.2±0.2°.

More preferably, the X-ray powder diffraction spectrum further comprises peaks at diffraction angles (2θ) of 8.7±0.2°, 13.4±0.2°, 13.6±0.2°, 19.6±0.2°, 21.6±0.2° and 26.6±0.2°.

Most preferably, the X-ray powder diffraction spectrum comprises substantially the same peaks at diffraction angles (2θ) as shown in FIG. 19, and the X-ray powder diffraction data are shown in Table 15:

TABLE 15

| 2θ (°) | intensity % |
|---|---|
| 6.2 | 12.7 |
| 8.4 | 20.3 |
| 8.7 | 28.7 |
| 9.8 | 7.9 |
| 12.1 | 11.2 |
| 12.6 | 6.2 |
| 13.4 | 26.3 |
| 13.6 | 22.7 |
| 14.3 | 22.1 |
| 15.0 | 19.0 |
| 16.3 | 8.7 |
| 16.8 | 60.9 |
| 17.5 | 12.6 |
| 18.0 | 6.0 |
| 18.7 | 5.3 |
| 19.1 | 78.3 |
| 19.3 | 100.0 |
| 19.6 | 37.1 |
| 20.3 | 11.0 |
| 20.7 | 12.8 |
| 21.6 | 26.1 |
| 21.9 | 56.8 |
| 22.1 | 59.1 |
| 23.2 | 50.7 |
| 23.7 | 17.6 |
| 24.4 | 43.1 |

TABLE 15-continued

| 2θ (°) | intensity % |
|---|---|
| 24.8 | 21.1 |
| 25.3 | 20.2 |
| 26.0 | 43.4 |
| 26.6 | 40.7 |
| 27.2 | 40.9 |
| 28.6 | 8.4 |
| 29.5 | 7.9 |
| 29.9 | 10.2 |
| 30.8 | 5.3 |
| 31.2 | 15.5 |
| 33.4 | 13.1 |
| 37.6 | 8.5 |

The invention provides a crystal form V of a mesylate of the compound of formula I having an X-ray powder diffraction spectrum comprising peaks at diffraction angles (2θ) of 25.2±0.2°, 9.3±0.2°, 16.6±0.2° and 19.1±0.2°.

Preferably, the X-ray powder diffraction spectrum further comprises peaks at diffraction angles (2θ) of 22.7±0.2°, 16.3±0.2°, 21.2±0.2°, 8.9±0.2° and 12.3±0.2°.

More preferably, the X-ray powder diffraction spectrum further comprises peaks at diffraction angles (2θ) of 23.7±0.2°, 20.0±0.2°, 15.9±0.2°, 24.6±0.2°, 28.6±0.2° and 25.5±0.2°.

Most preferably, the X-ray powder diffraction spectrum comprises substantially the same peaks at diffraction angles (2θ) as shown in FIG. 20, and, the X-ray powder diffraction data are shown in Table 16:

TABLE 16

| 2θ (°) | intensity % |
|---|---|
| 5.4 | 19.9 |
| 8.9 | 35.8 |
| 9.3 | 96.9 |
| 10.9 | 15.0 |
| 12.3 | 34.9 |
| 15.9 | 23.4 |
| 16.3 | 42.9 |
| 16.6 | 62.2 |
| 17.8 | 19.8 |
| 19.1 | 61.6 |
| 20.0 | 25.9 |
| 21.2 | 37.3 |
| 22.7 | 54.1 |
| 23.7 | 28.9 |
| 24.6 | 23.1 |
| 25.2 | 100.0 |
| 25.5 | 20.1 |
| 28.6 | 20.9 |
| 30.5 | 13.7 |

The invention provides a polymorph of a p-toluenesulfonate of the compound of formula I, comprising three crystal forms, referred to as crystal form I, crystal form II and crystal form III, respectively.

The invention provides a crystal form I of a p-toluenesulfonate of the compound of formula I having an X-ray powder diffraction spectrum comprising peaks at diffraction angles (2θ) of 13.0±0.2°, 15.4±0.2°, 24.3±0.2° and 25.7±0.2°.

Preferably, the X-ray powder diffraction spectrum further comprises peaks at diffraction angles (2θ) of 5.3±0.2°, 12.1±0.2°, 18.4±0.2°, 22.6±0.2° and 23.2±0.2°.

More preferably, the X-ray powder diffraction spectrum further comprises peaks at diffraction angles (2θ) of 14.6±0.2°, 16.9±0.2°, 18.8±0.2°, 19.9±0.2°, 25.3±0.2° and 29.3±0.2°.

Most preferably, the X-ray powder diffraction spectrum comprises substantially the same peaks at diffraction angles (2θ) as shown in FIG. 21, and the X-ray powder diffraction data are shown in Table 17:

TABLE 17

| 2θ (°) | intensity % |
|---|---|
| 5.3 | 37.0 |
| 8.6 | 12.9 |
| 12.1 | 27.0 |
| 12.5 | 20.9 |
| 13.0 | 100.0 |
| 14.1 | 7.0 |
| 14.6 | 23.5 |
| 15.4 | 55.0 |
| 16.9 | 22.9 |
| 17.2 | 11.7 |
| 18.4 | 26.3 |
| 18.8 | 22.8 |
| 19.6 | 16.0 |
| 19.9 | 25.4 |
| 20.5 | 13.9 |
| 21.3 | 21.9 |
| 22.6 | 40.5 |
| 23.2 | 40.5 |
| 23.4 | 13.1 |
| 24.3 | 79.4 |
| 25.3 | 22.6 |
| 25.7 | 56.9 |
| 26.5 | 21.1 |
| 28.1 | 10.8 |
| 29.3 | 23.1 |
| 30.1 | 7.0 |
| 30.9 | 13.4 |
| 33.0 | 9.0 |
| 33.2 | 8.2 |
| 37.3 | 8.6 |
| 38.4 | 6.0 |

The invention provides a crystal form II of a p-toluenesulfonate of the compound of formula I having an X-ray powder diffraction spectrum comprising peaks at diffraction angles (2θ) of 13.7±0.2°, 16.1±0.2°, 25.7±0.2° and 26.1±0.2°.

Preferably, the X-ray powder diffraction spectrum further comprises peaks at diffraction angles (2θ) of 11.0±0.2°, 14.6±0.2°, 17.0±0.2°, 22.8±0.2° and 26.5±0.2°.

More preferably, the X-rays powder diffraction spectrum further comprises peaks at diffraction angles (2θ) of 6.8±0.2°, 20.3±0.2°, 20.8±0.2°, 22.2±0.2°, 24.6±0.2° and 27.9±0.2°.

Most preferably, the X-ray powder diffraction spectrum comprises substantially the same peaks at diffraction angles (2θ) as shown in FIG. 22, and the X-ray powder diffraction data are shown in Table 18:

TABLE 18

| 2θ (°) | intensity % |
|---|---|
| 6.8 | 23.9 |
| 8.8 | 8.8 |
| 11.0 | 69.4 |
| 12.4 | 11.2 |
| 13.7 | 100.0 |
| 14.6 | 37.5 |
| 16.1 | 83.8 |
| 17.0 | 33.9 |
| 20.3 | 22.7 |
| 20.8 | 20.8 |
| 21.5 | 18.0 |
| 22.2 | 19.8 |
| 22.8 | 60.2 |

TABLE 18-continued

| 2θ (°) | intensity % |
|---|---|
| 24.6 | 20.4 |
| 25.7 | 74.2 |
| 26.1 | 95.5 |
| 26.6 | 42.6 |
| 27.9 | 21.4 |
| 30.7 | 13.0 |
| 31.2 | 16.1 |

The invention provides a crystal form III of a p-toluenesulfonate of the compound, of formula I having an X-ray powder diffraction spectrum comprising peaks at diffraction angles (2θ) of 8.2±0.2°, 14.4±0.2°, 25.9±0.2° and 26.3±0.2°.

Preferably, the X-ray powder diffraction spectrum further comprises peaks at diffraction angles (2θ) of 10.3±0.2°, 12.8±0.2°, 17.2±0.2°, 18.0±0.2° and 19.9±0.2°.

More preferably, the X-ray powder diffraction spectrum further comprises peaks at diffraction angles (2θ) of 4.8±0.2°, 13.2±0.2°, 15.1±0.2°, 19.3±0.2°, 24.2±0.2° and 24.5±0.2°.

Most preferably, the X-ray powder diffraction spectrum comprises substantially the same peaks at diffraction angles (2θ) as shown in FIG. 23, and the X-ray powder diffraction data are shown in Table 19:

TABLE 19

| 2θ (°) | intensity % |
|---|---|
| 4.8 | 25.3 |
| 6.3 | 19.0 |
| 8.2 | 72.1 |
| 8.6 | 10.5 |
| 9.8 | 11.3 |
| 10.0 | 18.1 |
| 10.3 | 31.2 |
| 11.3 | 12.0 |
| 12.8 | 43.1 |
| 13.2 | 23.5 |
| 14.4 | 100.0 |
| 15.1 | 23.1 |
| 17.2 | 46.5 |
| 18.0 | 45.0 |
| 18.7 | 17.4 |
| 19.3 | 24.8 |
| 19.9 | 34.3 |
| 21.2 | 15.3 |
| 22.4 | 13.9 |
| 22.9 | 17.9 |
| 23.9 | 13.2 |
| 24.2 | 24.9 |
| 24.5 | 28.3 |
| 25.0 | 16.4 |
| 25.3 | 21.8 |
| 25.9 | 63.2 |
| 26.3 | 48.3 |
| 27.8 | 20.3 |
| 28.8 | 14.6 |
| 31.0 | 10.1 |

The invention provides a polymorph of a 1,5-naphthalenedisulfonate of the compound of formula I, comprising three crystal forms, referred to as crystal form I, crystal form II and crystal form III, respectively.

The invention provides a crystal form I of a 1,5-naphthalenedisulfonate of the compound of formula I having an X-ray powder diffraction spectrum comprising peaks at diffraction angles (2θ) of 10.8±0.2°, 16.8±0.2°, 21.8±0.2° and 25.8±0.2°.

Preferably, the X-ray powder diffraction spectrum further comprises peaks at diffraction angles (2θ) of 10.2±0.2°, 16.0±0.2°, 19.1±0.2°, 20.8±0.2° and 26.7±0.2°.

More preferably, the X-ray powder diffraction spectrum further comprises peaks at diffraction angles (2θ) of 8.1±0.2°, 13.6±0.2°, 18.2±0.2°, 18.7±0.2°, 26.4±0.2° and 30.9±0.2°.

Most preferably, the X-ray powder diffraction spectrum comprises substantially the same peaks at diffraction angles (2θ) as shown in FIG. 24, and the X-ray powder diffraction data are shown in Table 20:

TABLE 20

| 2θ (°) | intensity % |
|---|---|
| 6.8 | 7.2 |
| 8.1 | 16.4 |
| 10.2 | 22.1 |
| 10.8 | 94.5 |
| 13.6 | 15.9 |
| 15.5 | 12.7 |
| 16.0 | 51.0 |
| 16.4 | 7.9 |
| 16.8 | 60.0 |
| 17.6 | 9.7 |
| 18.2 | 15.0 |
| 18.7 | 16.7 |
| 19.1 | 25.4 |
| 19.4 | 6.9 |
| 20.3 | 10.8 |
| 20.8 | 46.8 |
| 21.2 | 10.2 |
| 21.8 | 63.7 |
| 25.2 | 7.8 |
| 25.8 | 100.0 |
| 26.4 | 21.4 |
| 26.7 | 40.6 |
| 27.6 | 13.3 |
| 28.5 | 5.5 |
| 29.6 | 13.5 |
| 30.9 | 14.1 |
| 31.8 | 3.6 |
| 32.1 | 5.8 |
| 33.9 | 4.6 |
| 34.8 | 4.9 |

The invention provides a crystal form II of a 1,5-naphthalenedisulfonate of the compound of formula I having an X-ray powder diffraction spectrum comprising peaks at diffraction angles (2θ) of 4.2±0.2°, 16.4±0.2°, 22.8±0.2° and 27.3±0.2°.

Preferably, the X-ray powder diffraction spectrum also comprises peaks at diffraction angles (2θ) of 8.5±0.2°, 17.8±0.2°, 19.1±0.2°, 22.3±0.2° and 28.1±0.2°.

More preferably, the X-ray powder diffraction spectrum also comprises peaks at diffraction angles (2θ) of 10.4±0.2°, 13.5±0.2°, 15.1±0.2°, 21.2±0.2°, 24.0±0.2° and 26.5±0.2°.

Most preferably, the X-ray powder diffraction spectrum comprises substantially the same peaks at diffraction angles (2θ) as shown in FIG. 25, and the X-ray powder diffraction data are shown in Table 21:

TABLE 21

| 2θ (°) | intensity % |
|---|---|
| 4.2 | 100.0 |
| 8.5 | 19.4 |
| 10.4 | 12.7 |
| 13.5 | 11.2 |
| 15.1 | 7.9 |
| 16.4 | 60.9 |
| 17.8 | 18.5 |
| 19.1 | 14.0 |
| 21.2 | 5.4 |
| 22.3 | 22.2 |
| 22.8 | 40.2 |

TABLE 21-continued

| 2θ (°) | intensity % |
|---|---|
| 24.0 | 8.1 |
| 26.5 | 6.0 |
| 27.3 | 48.6 |
| 28.1 | 20.9 |
| 28.5 | 3.6 |
| 32.6 | 2.8 |

The invention provides a crystal form III of a 1,5-naphthalenedisulfonate of the compound of formula I having an X-ray powder diffraction spectrum comprising peaks at diffraction angles (2θ) of 13.0±0.2°, 22.7±0.2°, 24.1±0.2° and 25.7±0.2°.

Preferably, the X-ray powder diffraction spectrum further comprises peaks at diffraction angles (2θ) of 15.4±0.2° 18.8±0.2°, 23.2±0.2°, 25.4±0.2° and 26.5±0.2°.

More preferably, the X-ray powder diffraction spectrum further comprises peaks at diffraction angles (2θ) of 12.6±0.2°, 14.5±0.2°, 16.9±0.2°, 18.5±0.2°, 20.0±0.2° and 21.4±0.2°.

Most preferably, the X-ray powder diffraction spectrum comprises substantially the same peaks at diffraction angles (2θ) as shown in FIG. 26, and the X-ray powder diffraction data are shown in Table 22:

TABLE 22

| 2θ (°) | intensity % |
|---|---|
| 5.3 | 20.4 |
| 11.2 | 12.2 |
| 12.0 | 20.7 |
| 12.6 | 21.4 |
| 13.0 | 72.2 |
| 13.9 | 12.8 |
| 14.5 | 22.4 |
| 15.4 | 43.7 |
| 16.3 | 12.3 |
| 16.9 | 23.6 |
| 17.2 | 12.5 |
| 18.5 | 22.5 |
| 18.8 | 25.6 |
| 19.7 | 14.1 |
| 20.0 | 23.0 |
| 20.5 | 12.9 |
| 21.1 | 16.3 |
| 21.4 | 23.3 |
| 22.7 | 48.7 |
| 23.2 | 34.9 |
| 24.1 | 100.0 |
| 25.4 | 27.7 |
| 25.7 | 49.9 |
| 26.2 | 20.3 |
| 26.5 | 36.5 |
| 28.0 | 13.1 |
| 29.3 | 20.0 |
| 30.8 | 11.7 |
| 33.0 | 10.8 |
| 37.3 | 8.7 |

The term "substantially the same" related to X-ray diffraction peak position as used herein means to consider the typical peak position and intensity variability. For example, those skilled in the art will understand that the measured values of the peak positions (2θ) will be changed due to the different XRPD instruments, and sometimes this change may reach up to 0.2°. Moreover, those skilled in the art will understand that the preparation method of the XRPD sample, the XRPD instrument, the crystallinity of sample, the sample amount, the preferred orientation of the crystal and other factors will cause a change of relative peak intensity of the sample in the XRPD spectrum.

In another aspect, the invention provides a method for preparing a crystalline free base of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one, comprising the following steps of:

dissolving 9-((8-fluorine-6(1-methyl-1H-pyrazol-4-yl)-[1,2,4]triazolo[4,3-a]pyridin-3-yl)thio)-4-methyl-2H-[1,4]oxaazino[3,2-c]quinoline-3(4H)-one in an aqueous solvent, an organic solvent or a solvent mixture under heating, then cooling the solution or mixing the solution with an anti-solvent to obtain the crystalline free base; or evaporating a solution or suspension of 9((8-fluorine-6-(1-methyl-1H-pyrazol-4-yl)-[1,2,4]triazolo[4,3-a]pyridin-3-yl)thio)-4-methyl-2H-[1,4]oxaazino[3,2-c]quinoline-3(4H)-one rapidly or slowly to obtain the crystalline free base; or adding, an original compound solid or other solid particle additive as a heteronuclear crystal seed to a solution of 9-((8-fluorine-6-(1-methyl-1H-pyrazol-4-yl)-[1,2,4]triazolo[4,3a]pyridin-3-yl)thio)-4-methyl-2H-[1,4]oxaazino[3,2-c]quinoline-3(4H)-one to induce the crystalline free base; or dispersing 9-((8-fluorine-6-(1-methyl-1H-pyrazol-4-yl)-[1,2,4]triazolo[4,3-a]pyridin-3-yl)thio)-4-methyl-2H-[1,4]oxaazino[3,2-c]quinoline-3(4H)-one in an aqueous solvent, an organic solvent or a solvent mixture or an atmosphere of these media to obtain the crystalline free base; or heating, sublimating, grinding, freezing or fusing-cooling 9-((8-fluorine-6-methyl-1H-pyrazol-4-yl)-[1,2,4]triazolo[4,3-a]pyridin-3-yl)thio)-4-methyl-2H-[1,4]oxaazino[3,2-c]quinoline-3(4H)-one to obtain the crystalline free base; or combining the above methods to obtain the crystalline free base.

The present invention provides, but is not limited to, the following methods. For example, the organic solvent (if it exists) refers to, but is not limited to, the following solvents: alcohols, chloralkanes, ketones, ethers, cyclic ethers, esters, alkanes, cycloalkanes, benzenes, amides, sulfoxides or a mixture thereof, and preferably is selected from the group consisting of methanol, ethanol, n-propanol, isopropanol, n-butanol, acetonitrile, acetone, methyl ethyl ketone, tetrahydrofuran, dioxane, N,N-dimethylcarboxamide dimethyl sulfoxide, ethyl acetate, dichloromethane, trichloroethane, carbon tetrachloride, n-heptane, n-hexane, iso-octane, pentane, cyclohexane, cyclopentane, diethyl ether, methyltert-butyl ether, isopropyl ether, benzene, toluene, xylene and the mixture thereof; supercritical fluid such as liquid carbon dioxide, ionic liquid, polymer solution and the like.

For example:
1) Preparation of a Crystal Form I of the Free Base

A suitable solvent (including, but not limited to, isopropanol, isopropyl acetate, acetonitrile, tetrahydrofuran, 2-methoxyethanol or the mixture thereof) is added to a free base of the compound of formula I, and the free base is dispersed in the solvent to form a suspension (1-200 mg/mL). The suspension is stirred until the transformation into crystal form I of the free base is completed, and a solid-liquid separation is carried out to obtain crystal form I of free base.

2) Preparation of Crystal Form II of the Free Base

A suitable solvent (including, but not limited to, methanol, ethanol, acetone, dichlormethane or a mixture thereof) is added to a free base of the compound of formula I, and the free base is dispersed in the solvent to form a suspension (1-200 mg/mL). The suspension is stirred until transformation into crystal form II of the free base is completed, and a solid-liquid separation is carried out to obtain crystal form II of the free base.

3) Preparation of Crystal Form III of the Free Base

Acetonitrile is added to a free base of the compound of formula I, and the free base is dispersed in acetonitrile to form a suspension (1-200 mg/mL). The suspension is stirred at 40-60° C. until the transformation into crystal form III of the free base is completed, and a solid-liquid separation is carried out to obtain crystal form III of the free base.

4) Preparation of Crystal Form IV of the Free Base

A free base of the compound of formula I is heated to more than 100° C. (preferably more than 120° C.) and melted, and then slowly cooled to room temperature to obtain crystal form IV of the free base.

In another aspect, the invention provides a method for preparing a crystalline acid salt of 9-((8-fluoro-6-(1-methyl-1H-pyrazol-4-yl)-[1,2,4]triazolo[(4,3-a]pyridine-3-yl)thio)-4-methyl-2H-[1,4]oxaazido[3,2-c]quinoline-3(4H)-one, comprising the following steps of:

1) dissolving or dispersing a free base of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3 (4H)-one or dispersing in an aqueous solvent or a suitable organic solvent, then adding a liquid or solid inorganic acid or organic acid or a solution of inorganic acid or organic acid to the above system to obtain an acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one, or adding a free base solid of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one to an acid solution to obtain an acid salt of 9-((8-fluoro-6-(1-methyl-1H-pyrazol-4-yl)-[1,2,4]triazolo[(4,3-a]pyridine-3-yl)thio)-4-methyl-2H-[1,4]oxaazido[3,2-c]quinoline-3(4H)-one;

2) collecting the solid product precipitated during the salt-forming process, or obtaining the solid product by creating supersaturation of the salt-forming system to prepare the crystalline acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one, wherein a method for creating supersaturation comprises evaporation of solvent, or addition of an anti-solvent, or a cooling method;

and/or, transforming one crystal form of the acid salt into another crystal form of the acid salt by a crystal transformation method, wherein the crystal transformation method comprises heating or a crystal transformation method of a suspension in a suitable solvent;

wherein the suitable organic solvent of the salt-forming process in step 1) is selected from the group consisting of alcohols, chloralkanes, ketones, ethers, cyclic ethers, esters, alkanes, cycloalkanes, benzenes, amides, sulfoxides and a mixture thereof, preferably methanol, ethanol, n-propanol, isopropanol, acetonitrile, acetone, 1,4-dioxane, tetrahydrofuran, N,N-dimethylcarboxamide, ethyl acetate, isopropyl acetate, 2-methoxyethyl ether and a mixture thereof;

wherein the "acid salt" used herein refers to a suitable, pharmaceutically acceptable salt which is thrilled by a compound of the present invention and an acid substance, wherein the acid salt comprises an inorganic acid salt or an organic acid salt; wherein the inorganic acid salt is preferably selected from the group consisting of hydrochloride, sulfate, hydrobromide, hydrofluoride, hydroiodide and phosphate, more preferably hydrochloride, sulfate and phosphate; wherein the organic acid salt is preferably selected from the group consisting of 2,5-dihydroxybenzeneformate, 1-hydroxy-2-naphthaleneformate, acetate, dichloroacetate, trichloroacetate, acetohydroxamate, adipate, benzene sulfonate, 4-chlorobenzene sulfonate, benzeneformate, 4-acetamidobenzeneformate, 4-aminobenzeneformate, caprate, caproate, caprilate, cinnamoate, citrate, cyclohexylsulfamate, camphorsulfonate, aspartate, camphorate, gluconate, glucuronate, glutamate, erythorbate, lactate, aspartate, malate, mandelate, pyroglutamate, tartrate, lauryl sulfate, dibenzoyltartrate, ethyl-1,2-disulfonate, esylate, formate, famarate, galactonate, gentisate, glutarate, 2-oneglutamate, glycollate, hippurate, isethionate, lactobionate, ascorbate, aspartate, laurate, camphorate, maleate, malonate, mesylate, 1,5-naphthalenedisulfonate, naphthalene-2-sulfonate, nicotinate, oleate, orotate, oxalate, palmitate, embonate, propionate, salicylate, 4-aminosalicylate, sebacate, stearate, butanedioate, thiocyanate, undecylenate, trifluoroacetate, succinate, and p-toluenesulfonate, more preferably mesylate, p-toluenesulfonate and 1,5-naphthalenedisulfonate.

For example:

1) Preparation of Crystal Form I of a Hydrochloride Salt

A suitable solvent (including, but not limited to, methanol, acetonitrile, acetone, ethyl acetate and a mixture thereof) is added to a free base of the compound of formula I, then an equal or excess molar equivalent of hydrochloric acid is added. The mixture is stirred, and after the salt-forming reaction is completed, a solid-liquid separation is carried out to obtain crystal form I of the hydrochloride salt.

2) Preparation of Crystal Form of a Sulfate Salt

A suitable solvent (including, but not limited to, acetonitrile, acetone and a mixture thereof) is added to a free base of the compound of formula I, then an equal or excess molar equivalent of sulfuric acid is added. The mixture is stirred, and after the salt-forming reaction is completed, a solid-liquid separation is carried out to obtain crystal form I of the sulfate salt.

3) Preparation of Crystal Form of a Sulfate Salt

An ethanol-water solution with a volume ratio of 5%-95% is added to a free base of the compound of formula I, then an equal or excess molar equivalent of sulfuric acid is added. The mixture is stirred, and after the salt-forming reaction is completed, a solid-liquid separation is carried out to obtain crystal form II of the sulfate salt.

4) Preparation of Crystal Form I of a Phosphate Salt

Methanol or an ethanol-water solution with a volume ratio of 5%-95% is added to a free base of the compound of formula I, then an equal or excess molar equivalent of phosphoric acid is added. The mixture is stirred, and after the salt-forming reaction is completed, a solid-liquid separation is carried out to obtain crystal form I of the phosphate salt.

5) Preparation of Crystal Form II of a Phosphate Salt

A suitable solvent (including, but not limited to, acetonitrile, ethyl acetate, tetrahydrofuran and a mixture thereof) is added to a free base of the compound of formula I, then an equal or excess molar equivalent of phosphoric acid is added. The mixture is stirred, and after the salt-forming reaction is completed, a solid-liquid separation is carried out to obtain crystal form II of the phosphate salt.

6) Preparation of Crystal Form III of a Phosphate Salt

A suitable solvent (including, but not limited to acetone) is added to a free base of the compound of formula I, then an equal or excess molar equivalent of phosphoric acid is added. The mixture is stirred, and after the salt-forming reaction is completed, a solid-liquid separation is carried out to obtain crystal form III of the phosphate salt.

7) Preparation of Crystal Form IV of a Phosphate Salt

A suitable solvent (including, but not limited to methanol) is added to a free base of the compound of formula I, then an equal or excess molar equivalent of phosphoric acid is added. The mixture is stirred, and after the salt-forming reaction is completed, a solid-liquid separation is carried out to obtain crystal form IV of the phosphate salt.

8) Preparation of Crystal Form I of a Mesylate Salt

A suitable solvent (including, but not limited to, acetone, tetrahydrofuran, isopropyl acetate, ethyl acetate, 2-methoxyethyl ether, 1,4-dioxane and a mixture thereof) is added to a free base of the compound of formula I, then an equal or excess molar equivalent of methanesulfonic acid is added. The mixture is stirred, and after the salt-forming reaction is completed, a solid-liquid separation is carried out to obtain crystal form I of the mesylate salt.

9) Preparation of Crystal Form II of a Mesylate Salt

A methanol-water solution with a volume ratio of 5%-95% is added to a free base of the compound of formula I, then the mixture is stirred. An equal or excess molar equivalent of methanesulfonic acid is added until the solution is clear. After mesylate is precipitated, a solid-liquid separation is carried out to obtain crystal form II of the mesylate salt.

10) Preparation of Crystal Form of a Mesylate Salt

Methanol is added to a free base of the compound of formula I, then an equal or excess molar equivalent of methanesulfonic acid is added slowly. After the compound is dissolved, a seed crystal of crystal form III of the mesylate salt is added immediately. The mixture is stirred, and after the salt-forming reaction is completed, a solid-liquid separation is carried out to obtain crystal form III of the mesylate salt.

Alternatively, in the absence of a crystal seed, crystal form IV of the mesylate salt is obtained first, then crystal form IV of mesylate is dried in a vacuum at 100-120° C. overnight, and crystal form IV of the mesylate salt is transformed into crystal form III of the mesylate salt.

Alternatively, crystal form V of the mesylate salt is dispersed in a single or mixed anti-solvent, such as n-heptane/ethyl acetate solution. Then, the mixture is stirred at room temperature or under heating, and crystal form V of the mesylate salt is transformed into crystal form III of the mesylate salt.

11) Preparation of Crystal Form IV of a Mesylate Salt

Methanol is added to a free base of the compound of formula I, then an equal or excess molar equivalent of methanesulfonic acid is added. The mixture is stirred, and after the salt-forming reaction is completed, a solid-liquid separation is carried out to obtain crystal form IV of the mesylate salt.

12) Preparation of Crystal Form V of a Mesylate Salt

Dimethyl sulfoxide (DMSO) is added to a free base of the compound of formula I, then an equal or excess molar equivalent of methanesulfonic acid is added. The mixture is stirred, and after the salt-forming reaction is completed, a suitable amount of ethyl acetate is added and the stirring is continued. Then, a solid-liquid separation is carried out to obtain crystal form V of the mesylate salt.

13) Preparation of Crystal Form I of a p-toluenesulfonate Salt

A suitable solvent (including, but not limited to, methanol, acetonitrile, acetone and ar mixture thereof) is added to a free base of the compound of formula I, then an equal or excess molar equivalent of p-toluenesulfonic acid is added. The mixture is stirred, and after the salt-forming reaction is completed, a solid-liquid separation is carried out to obtain crystal form I of p-toluenesulfonate.

14) Preparation of Crystal Form II of a p-toluenesulfonate Salt

A suitable solvent (including, but not limited to ethyl acetate) is added to a free base of the compound of formula I, then an equal or excess molar equivalent of p-toluenesulfonic acid is added. The mixture is stirred, and after the salt-forming reaction is completed, a solid-liquid separation is carried out to obtain crystal form II of p-toluenesulfonate.

15) Preparation of Crystal Form III of a p-toluenesulfonate Salt

An ethanol-water solution with a volume ratio of 5%-95% is added to a free base of the compound of formula I, then an equal or excess molar equivalent of p-toluenesulfonic acid is added. The mixture is stirred, and after the salt-forming reaction is completed, a solid-liquid separation is carried out to obtain crystal form III of p-toluenesulfonate.

16) Preparation of Crystal Form I of a 1,5-Naphthalenedisulfonate Salt

A suitable solvent (including, but not limited to, methanol, acetonitrile, acetone and is a mixture thereof) is added to a free base of the compound of formula I, then an equal or excess molar equivalent of 1,5-naphthalenedisulfonic acid is added. The mixture is stirred, and after the salt-forming reaction is completed, a solid-liquid separation is carried out to obtain crystal form I of the 1,5-naphthalenedisulfonate salt.

17) Preparation of Crystal Form II of a 1,5-Naphthalenedisulfonate Salt

A suitable solvent (including, but not limited to ethyl acetate) is added to a free base of the compound of formula I, then an equal or excess molar equivalent of 1,5-naphthalenedisulfonic acid is added. The mixture is stirred, and after the salt-forming reaction is completed, a solid-liquid separation is carried out to obtain crystal form II of the 1,5-naphthalenedisulfonate salt.

18) Preparation of Crystal Form III of a 1,5-naphthalenedisulfonate Salt

A suitable solvent (including, but not limited to methanol) is added to a free base of the compound of formula I, then an equal or excess molar equivalent of 1,5-naphthalenedisulfonic acid is added. The mixture is stirred, and after the salt-forming reaction is completed, a solid-liquid separation is carried out to obtain crystal form III of the 1,5-naphthalenedisulfonate salt.

It should be noted that those skilled in the art will understand that the technical solution of the invention may be modified or equivalently varied, and such modifications and variations, for example, the organic solvent which is exemplified in the foregoing part of the present invention, also include the spirit and scope of the present invention, and are considered to be within the scope of the present invention.

In another aspect, the invention provides a pharmaceutical composition comprising a therapeutically effective amount of a crystalline free base or a crystalline acid salt of the compound of formula I, and a pharmaceutically acceptable carrier or excipient.

In another aspect, the invention provides a use of the above crystalline free base or polymorph thereof, the above crystalline acid salt or polymorph thereof of the compound of formula I, or the above pharmaceutical composition in the preparation of a medicament for the treatment of a protein kinase-related disease, wherein the protein kinase is selected from the group consisting of C-Met and VEGFR receptor tyrosine kinase.

In another aspect, the invention provides a method for modulating a catalytic activity of a protein kinase, comprising a step of contacting the protein kinase with the above crystalline free base or polymorph thereof, the above crystalline acid salt or polymorph thereof of the compound of formula I, or the above pharmaceutical composition, wherein the protein kinase is selected from the group consisting of C-Met and VEGFR receptor tyrosine kinase.

In another aspect, the invention provides a use of the above crystalline free base or polymorph thereof, the above crystalline acid salt or polymorph thereof of the compound of formula I, or the above pharmaceutical composition in the preparation of a medicament for the treatment of cancer and metastasis, including cancer (solid tumor), hematopoietic tumor of the lymphatic system, hematopoietic tumor of the bone marrow system, mesenchymal tumor, central and peripheral nervous system tumor and other tumor. In non-limiting embodiments, the cancer is selected from the group consisting of bladder cancer, breast cancer, colon cancer, kidney cancer, liver cancer, stomach cancer, lung cancer (non-small cell lung cancer) and skin cancer; the hematopoietic tumor of the lymphatic system is selected from the group consisting of leukemia, acute lymphocytic leukemia and chronic lymphocytic leukemia; the hematopoietic tumor of the bone marrow system is selected from the group consisting of acute or chronic myelogenous leukemia, myelodysplastic syndrome and promyelocytic leukemia; and the mesenchymal tumor is selected from the group consisting of fibrosarcoma, rhabdomyosarcoma, soft tissue sarcoma and osteosarcoma; the central and peripheral nervous system tumor is selected from the group consisting of astrocytoma, neuroblastoma, glioma and nerve ending tumor; and the other tumor is selected from the group consisting of malignant melanoma, seminoma, teratocarcinoma, thyroid follicular cancer and Kaposi's sarcoma.

Preferably, the invention provides a use of the above crystalline free base or polymorph thereof, the above crystalline acid salt or polymorph thereof of the compound of formula I, or the above pharmaceutical composition in the preparation of a medicament for the treatment of liver cancer, lung cancer, breast cancer, squamous cell carcinoma of the skin and stomach cancer.

A "pharmaceutical composition" as used herein means a mixture comprising one or more compounds described in the present invention or physiologically/pharmaceutically acceptable salts or prodrugs thereof, and optionally comprising other components such as physiologically/pharmaceutically acceptable carriers and excipients. The purpose of a pharmaceutical composition is to facilitate administration of a compound to an organism, which is conducive to the absorption of the active ingredient, thereby displaying biological activity.

PREFERRED EMBODIMENTS

Figure 1:
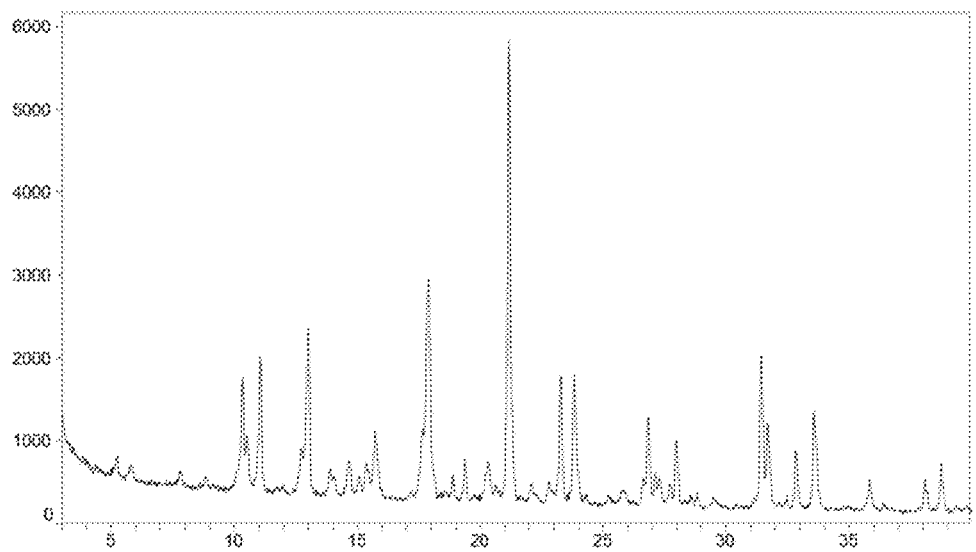
FIG. 1 is the X-ray powder diffraction spectrum of crystal form I of the free base of the compound of formula I: the abscissa is angle 2θ (°), and the ordinate is intensity.

The following specific examples are used to further describe the particular aspects of the solutions of the invention, but these examples are not intended to limit the scope of the invention in any way.

Methods and Materials

The crystal forms of free base of the compound of formula I and salt crystal forms thereof were characterized by their X-ray powder diffraction (XRPD) spectra. Therefore, the X-ray powder diffraction spectrum of the mentioned salt was collected by a Bruker D8 Discover X-ray powder diffractometer with GADDS (General Area Detector Diffraction System) CS using Cu Kα radiation (1.54 Å) in reflective mode. Tube voltage and current amount were set to 40 kV and 40 mA, respectively. In the 2θ range of 3.0° to 40° or 45°, the sample was scanned for 60 seconds. For peak position represented by 2θ, a corundum standard was used to calibrate the diffractometer. All analysis was usually implemented at 20° C.-30° C. room temperature. The data was collected and integrated by GADDS using WNT software version 4.1.14T The diffraction spectrum was analyzed by DiffracPlus software with version 9.0.0.2 Eva, which was published in 2003. The sample of XRPD was prepared as follows: The sample was placed on a monocrystalline silicon wafer, then the sample powder was pressed by a glass sheet or an equivalent to ensure that the surface of the sample was flat and had a suitable height. Then, the sample holder was placed in the Bruker XRPD instrument, and the X-ray powder diffraction spectrum was collected using the above instrument parameters. The measured difference related to the analysis result of the X-ray powder diffraction was produced by various factors including: (a) the error of sample preparation (e.g., sample height), (b) the instrument error, (c) the calibration error, (d) operator error (including those errors that occur in the determination of peak positions), and (e) properties of the substance (e.g. preferred orientation error). Calibration error and sample height error often lead to shifts of all the peaks in the same direction. In general, the calibration factor will make the measured peak positions inconsistent with the expected peak positions and in the range of 2θ expected values±0.2°. Angle 2θ values (°) and intensity values (% relative to the highest peak value) of each polymorph obtained in the Examples of the present invention are shown in Tables 1 to 22.

Preparation of Amorphous Free Base

The amorphous free base of the compound of formula I was prepared according to Example 22 of Chinese Patent Application. CN201310173581.4 and the PCT application thereof (PCT/CN2014/072825). The specific procedure used was as follows: To a 30 mL microwave tube, 8-fluoro-6-(1-methyl-1H-pyrazol-4-yl)-[1,2,4]triazolo[4,3-a]pyridin-3-thiol (93 mg, 0.375 mmol), 9-bromo-4-methyl-2H-[1,4]oxazino[3,2-c]quinolin-3(4H)-one (100 mg, 0.341 mmol), tris(dibenzylideneacetone)dipalladium (20 mg, 0.034 mmol), 4,5-bis(diphenylphosphino)-9,9-dimethyxanthene (40 mg, 0.068 mmol), sodium tert-butoxide (40 mg, 0.409 mmol) and anhydrous N,N-dimethylformamide (5 mL) were added successively. The reaction mixture was purged with $N_2$ and heated by microwaves to 120° C. for 4 hours. After the reaction was stopped, N,N-dimethylformamide was removed by rotary evaporation. The residue was purified by reverse phase column chromatography to obtain 36 mg white amorphous 9-((8-fluoro-6-(1-methyl-1H-pyrazol-4-yl)-[1,2,4]triazolo[4,3-a]pyridin-3-yl)thio)-4-methyl-2H-[1,4]oxazino[3,2-c]quinolin-3(4H)-one 22.

Solubility of Amorphous Free Base in Different Simulated Biological Media

Procedure: About 10 mg of amorphous free base was weighed and placed in a 2 mL glass vial. Then, 1 mL of simulated biological media (simulated artificial gastric juice, simulated artificial intestinal juice-fasting, and simulated artificial intestinal juice-satiety), and a magnetic stirrer were added, and then the vial was sealed. The mixture was magnetically stirred at 37° C. and about 0.4 mL of the sample was taken at different time points. The mixture was filtered with a centrifuge tube (pore size of filter membrane: 0.45 μm), the filtrate was taken and the content of the compound of formula I therein was analyzed by HPLC. Measurement results are shown in the table below:

| Crystal Form | Simulated biological media | Solubility (1 hour) mg/mL | Solubility (4 hours) mg/mL | Solubility (22 hours) mg/mL |
| --- | --- | --- | --- | --- |
| Amorphous free base | Simulated artificial gastric juices | 0.011 | 0.009 | 0.009 |
| | Simulated artificial intestinal juice-fasting | 0.002 | 0.002 | 0.002 |
| | Simulated artificial intestinal juice-satiety | 0.003 | 0.002 | 0.002 |

Example 1: Preparation of Crystal Form I of the Free Base

A certain amount of free base of the compound of formula I (amorphous) was weighed and placed in a container. A solvent was added and the free base of the compound of formula I was dispersed in the solvent to form a suspension (1-200 mg/mL). The suspension was stirred at room temperature (20-25° C.) until the amorphous compound of formula I was transformed into crystal form I of the free base. A solid-liquid separation was carried out to obtain a solid, i.e., crystal form 1 of the free base. The X-ray powder diffraction spectrum is shown in FIG. 1.

Figure 2:
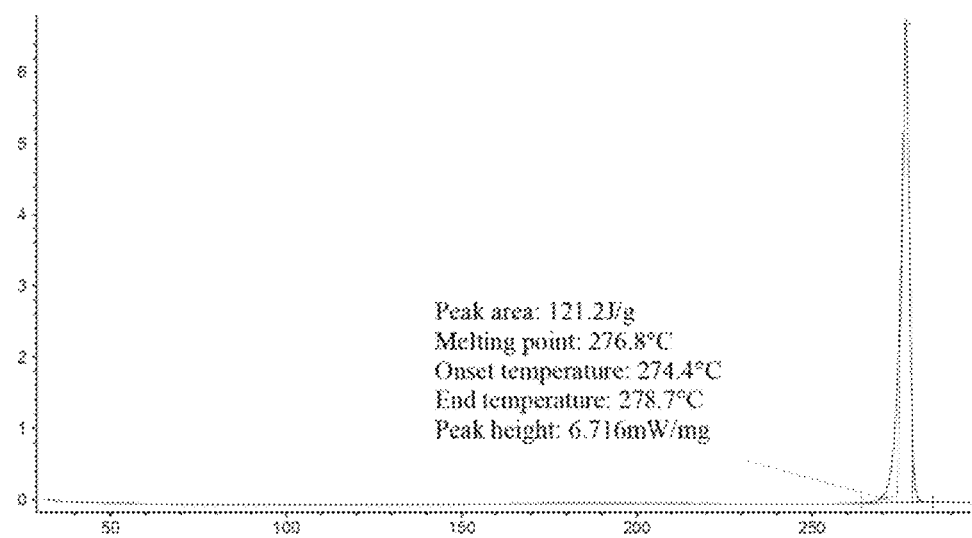
FIG. 2 is the differential scanning calorimetry (DSC) spectrum of crystal form I of the free base of the compound of formula I; the abscissa is temperature (° C.), and the ordinate is heat flow (W/g); the exothermic peak is downward; wherein the peak area of the peak shown is 121.2 J/g, the melting point is 276.8° C., the onset temperature is 274.4° C., the end temperature is 278.7° C., and the peak height is 6.716 mW/mg.
Figure 3:
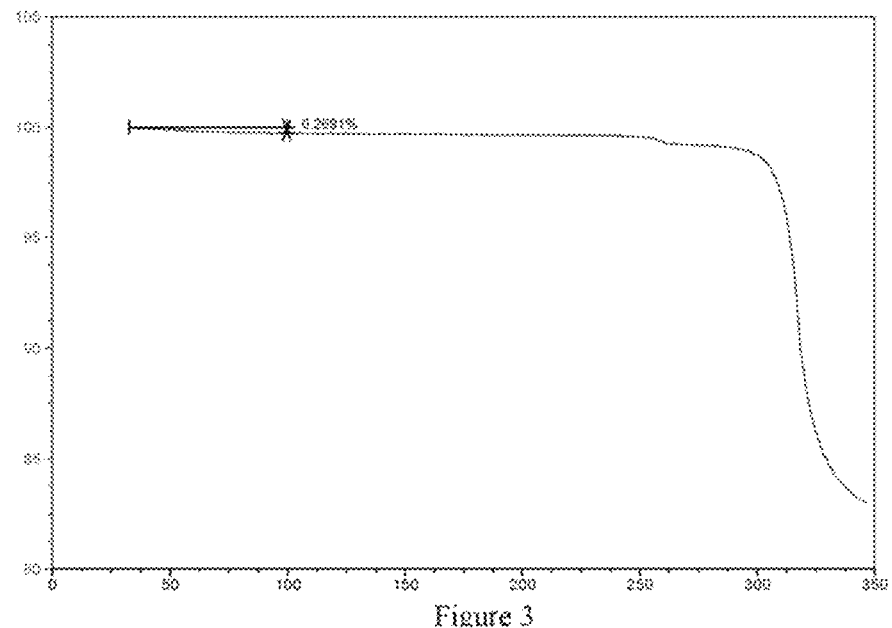
FIG. 3 is the thermogravimetric analysis (TGA) spectrum of crystal form I of the free base of the compound of formula I; the abscissa is temperature (° C.), and the ordinate is weightlessness ratio (%)

The melting point of crystal form I of the free base was measured by a differential scanning calorimetry (DSC, model: Neszsch DSC 204 F1). Measurement conditions: heating from room temperature to 300° C. at a heating rate of 10° C. per minute in a nitrogen atmosphere and a nitrogen flow rate of 20 mL per minute. The DSC spectrum of crystal form I of the free base is shown in FIG. 2. The melting point of crystal form I of the free base (onset temperature) was 274.4° C. The thermal weightlessness of crystal form I of the free base was measured by a thermal gravimetric analyzer (TGA, model: TA Q500). Measurement conditions: heating from room temperature to 350° C. at a heating rate of 10° C. per minute in a nitrogen atmosphere and a nitrogen flow rate of 50 mL per minute. The TGA spectrum of crystal form I of the free base is shown in FIG. 3. Due to almost no weight loss below 100° C., it was determined that crystal form I of the free base is an anhydrous compound.

| Initial state of the compound of formula I | Amorphous | Amorphous | Amorphous | Amorphous | Amorphous | Amorphous | Amorphous |
| --- | --- | --- | --- | --- | --- | --- | --- |
| Amount of the compound of formula I | 20 mg | 20 mg | 20 mg | 20 mg | 20 mg | 20 mg | 20 mg |
| Solvent name | Isopropanol | Isopropyl acetate | Acetonitrile | Tetrahydrofuran | 2-methoxyethanol | Isopropanol | Isopropyl acetate | Isopropanol | Acetonitrile |
| Solvent amount | 1 mL | 1 mL | 1 mL | 1 mL | 1 mL | 0.5 mL | 0.5 mL | 0.5 mL | 0.5 mL |
| Concentration | 20 mg/mL | 20 mg/mL | 20 mg/mL | 20 mg/mL | 20 mg/mL | Total concentration of mixed solvent | Total concentration of mixed solvent |
| Experimental temperature | Room temperature | Room temperature | Room temperature | Room temperature | Room temperature | Room temperature | Room temperature |
| Experimental results | Crystal Form I | Crystal Form I | Crystal Form I | Crystal Form I | Crystal Form I | Crystal Form I | Crystal Form I |

Solubility of Crystal Form I of Free Base in Different Simulated Biological Media Procedure: About 10 mg of crystal form I of free base was weighed and placed in a 2 mL glass vial, 1 mL of simulated biological media (simulated artificial gastric juice, simulated artificial intestinal juice-fasting, and simulated artificial intestinal juice-satiety), and a magnetic stirrer was added, then the vial was sealed. The mixture was magnetically stirred at 37° C. and about 0.4 mL of the sample was taken at different time points. The mixture was filtered with a centrifuge tube (pore size of filter membrane: 0.45 μm), the filtrate was taken and the content of the compound of formula I therein was analyzed by HPLC. Measurement results were shown in the table below:

| Crystal Form | Simulated biological media | Solubility (1 hour) mg/mL | Solubility (4 hours) mg/mL | Solubility (22 hours) mg/mL |
|---|---|---|---|---|
| Crystal form I of free base | Simulated artificial gastric juices | 0.018 | 0.019 | 0.019 |
| | Simulated artificial intestinal juice-fasting | 0.001 | 0.001 | 0.002 |
| | Simulated artificial intestinal juice-satiety | 0.004 | 0.004 | 0.004 |

Example 2: Preparation of Crystal Form II of the Free Base

Figure 4:
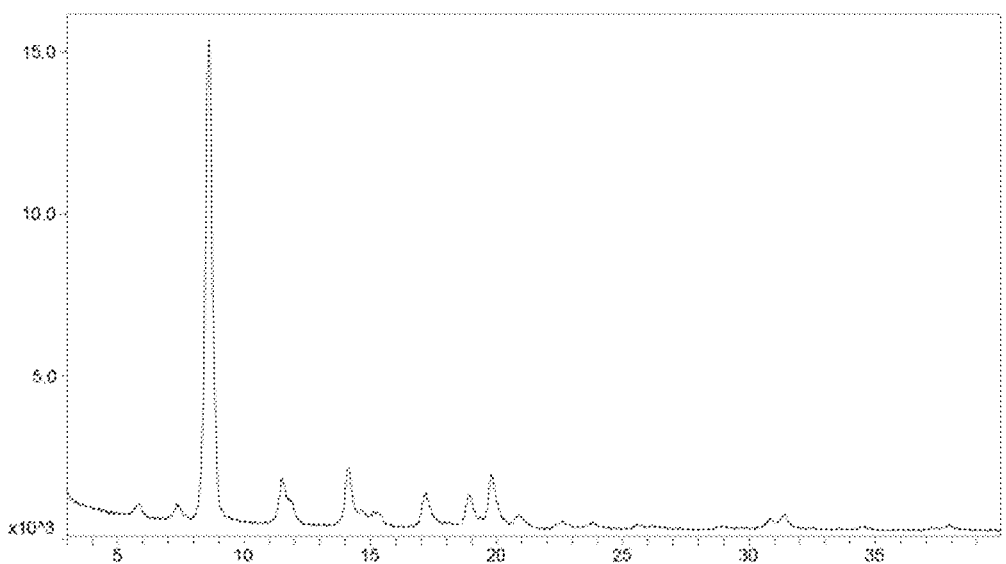
FIG. 4 is the X-ray powder diffraction spectrum of crystal form II of the free base of the compound of formula I; the abscissa is angle 2θ (°), and the ordinate is intensity.

A certain amount of free base of the compound of formula I (amorphous) was weighed and placed in a container. A solvent was added and the free base of the compound of formula I was dispersed in the solvent to form a suspension (1-200 mg/mL). A suitable solvent was added. The suspension was stirred at room temperature (20-25° C.) until the amorphous compound of formula I was transformed to crystal form II of the free base. A solid-liquid separation was carried out to obtain a solid, i.e., crystal in form II of the free base, and its X-ray powder diffraction spectrum is shown in FIG. 4.

Example 3: Preparation of Crystal Form III of the Free Base

Figure 5:
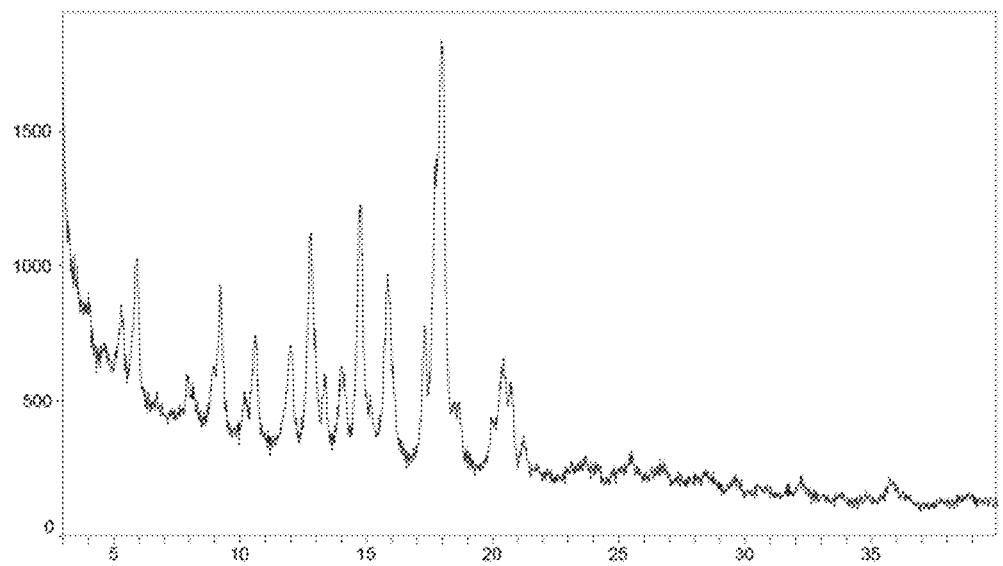
FIG. 5 is the X-ray powder diffraction spectrum of crystal form III of the free base of the compound of formula I; the abscissa is angle 2θ (°), and the ordinate is intensity.

About 20 mg of crystal form II of the free base of the compound of formula I was weighed and placed in a 2 mL HPLC vial, 1.0 of acetonitrile was added, the mixture was magnetically stirred for about 1 day at 50° C., and sufficiently crystallized to obtain a solid compound, i.e., crystal form III of the free base. Its X-ray powder diffraction spectrum is shown in FIG. 5.

Figure 6:
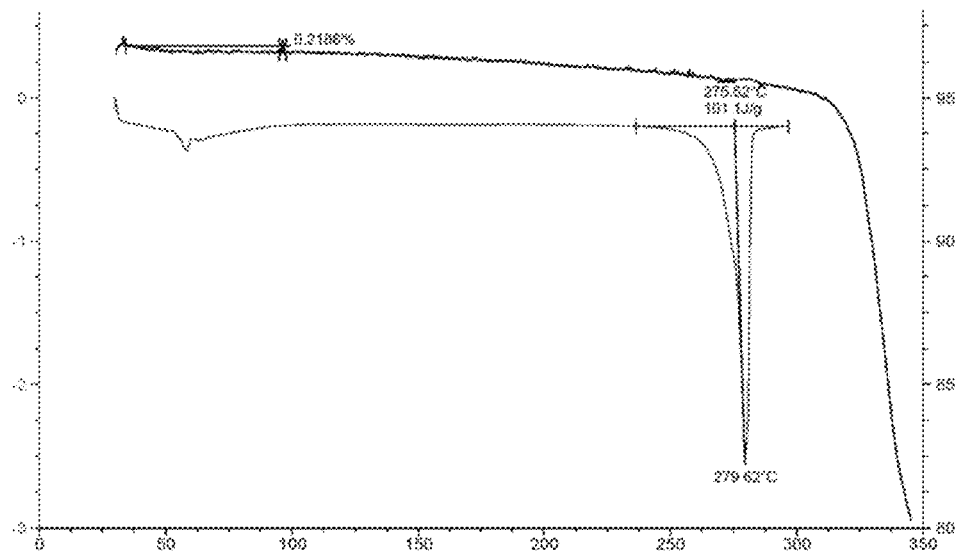
FIG. 6 is the DSC/TGA stacking spectrum of crystal form III of the free base of the compound of formula I; the abscissa is temperature (° C.), the left ordinate is heat flow (W/g), and the exothermic peak is upward; and the right ordinate is weightlessness ratio (%)

The melting point of crystal form III of the free base was measured by differential scanning calorimetry (DSC, model: TA Q2000). Measurement conditions: heating from room temperature to 300° C. at a heating rate of 10° C. per minute in a nitrogen atmosphere and a nitrogen flow rate of 20 mL per minute. The DSC spectrum of crystal form III of the free base is shown in FIG. 5. The melting point of crystal form III of the free base (onset temperature) was 275.5° C. The thermal weightlessness of crystal form III of the free base was measured by a thermal gravimetric analyzer (TGA, model: TA Q500). Measurement conditions: heating from room temperature to 350° C. at a heating rate of 10° C. per minute in a nitrogen atmosphere and a nitrogen flow rate of 50 mL per minute. The TGA spectrum of crystal form III of the free base was shown in FIG. 6. Due to almost no weight loss below 100° C., it was determined that crystal form III of the free base is an anhydrous compound.

Solubility of Crystal Form III of the Free Base in Different Simulated Biological Media Procedure: About 10 mg of crystal form of the free base was weighed and placed in a 2 mL glass vial. Then, 1 mL of simulated biological media (simulated artificial gastric juice, simulated artificial intestinal juice-fasting, and simulated artificial intestinal juice-satiety), and a magnetic stirrer were added, and the vial was sealed. The mixture was magnetically stirred at 37° C. and about 0.4 mL of the sample was taken at different time points. The mixture was filtered with a centrifuge tube (pore size of filter membrane: 0.45 μm), the filtrate was taken and the content of the compound of formula I therein was analyzed by HPLC. Measurement results are shown in the table below:

| | | | | | | | | |
|---|---|---|---|---|---|---|---|---|
| Initial state of the compound of formula I | Amorphous | Amorphous | Amorphous | Amorphous | Amorphous | Amorphous | Amorphous | |
| Amount of the compound of formula I | 20 mg | 20 mg | 20 mg | 20 mg | 20 mg | 20 mg | 20 mg | |
| Solvent name | Isopropanol | Isopropyl acetate | Acetonitrile | Tetrahydrofuran | 2-methoxyethanol | Isopropanol | Isopropyl acetate | Isopropanol | Acetonitrile |
| Solvent amount | 1 mL | 1 mL | 1 mL | 1 mL | 1 mL | 0.5 mL | 0.5 mL | 0.5 mL | 0.5 mL |
| Concentration | 20 mg/mL | 20 mg/mL | 20 mg/mL | 20 mg/mL | 20 mg/mL | Total concentration of mixed solvent | Total concentration of mixed solvent | |
| Experimental temperature | Room temperature | Room temperature | Room temperature | Room temperature | Room temperature | Room temperature | Room temperature | |
| Experimental results | Crystal Form II | Crystal Form II | Crystal Form II | Crystal Form II | Crystal Form II | Crystal Form II | Crystal Form II | |

| Crystal Form | Simulated biological media | Solubility (1 hour) mg/mL | Solubility (4 hours) mg/mL | Solubility (22 hours) mg/mL |
|---|---|---|---|---|
| Crystal form III of free base | Simulated artificial gastic juices | 0.040 | 0.043 | 0.043 |
| | Simulated artificial intestinal juice-fasting | 0.004 | 0.004 | 0.004 |
| | Simulated artificial intestinal juice-satiety | 0.011 | 0.011 | 0.010 |

Example 4: Preparation of Crystal Form IV of the Free Base

Figure 7:
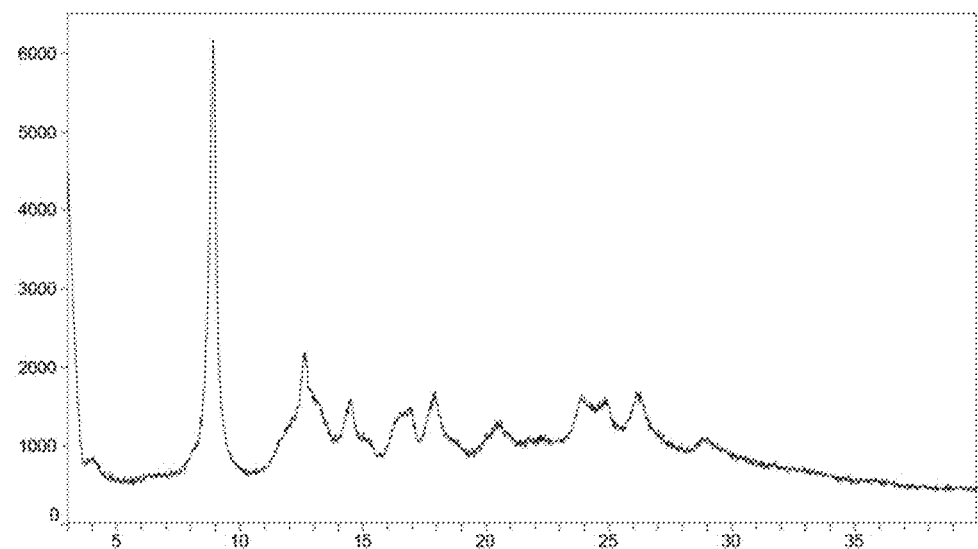
FIG. 7 is the X-ray powder diffraction spectrum of crystal form IV of the free base of the compound of formula I; the abscissa is angle 2θ (°), and the ordinate is intensity.

About 10 mg of crystal form II of the free base of the compound of formula I was weighed and placed in a TGA (Thermal gravimetric analyzer, model: TA Q500), and then heated from room temperature 25° C. to 120° C. at a rate of 10° C./min to remove the solvent, and then cooled slowly to room temperature (10° C./min) to obtain a solid. Its X-ray powder diffraction spectrum is shown in FIG. 7.

Example 5: Preparation of Crystal Form I of a Hydrochloride Salt

Figure 8:
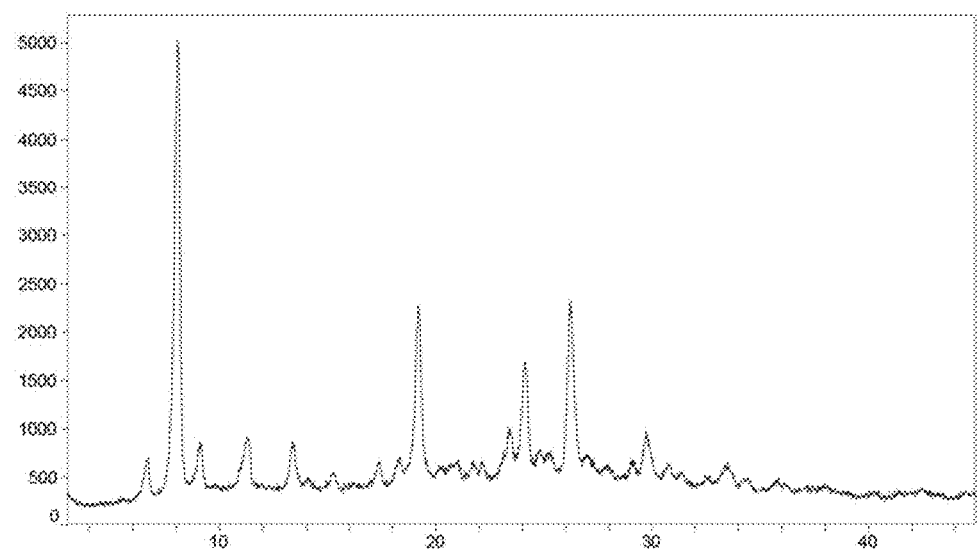
FIG. 8 is the X-ray powder diffraction spectrum of crystal form I of a hydrochloride salt of the compound of formula I; the abscissa is angle 2θ (°), and the ordinate is intensity.

About 20 mg of free base of the compound of formula I was weighed and placed in a 2 mL HPLC vial. Then, 1.0 mL of methanol was added, and then 4.8 μL of 37% hydrochloric acid solution were added. The mixture was magnetically stirred for about 2 days at room temperature and sufficiently crystallized to obtain crystal form I of the hydrochloride salt. Its X-ray powder diffraction spectrum is shown in FIG. 8.

| Initial state of the compound of formula I | Free base | Free base | Free base | Free base |
|---|---|---|---|---|
| Amount of the compound of formula I | 20 mg | 20 mg | 20 mg | 20 mg |
| Solvent name | Methanol | Isopropyl acetate | Acetonitrile | Acetone |
| Solvent amount | 1 mL | 1 mL | 1 mL | 1 mL |
| Concentration | 20 mg/mL | 20 mg/mL | 20 mg/mL | 20 mg/mL |
| 37% HCl | 4.8 μL | 4.8 μL | 4.8 μL | 4.8 μL |
| Experimental temperature | Room temperature | Room temperature | Room temperature | Room temperature |
| Experimental results | Crystal form I of hydrochloride | Crystal form I of hydrochloride | Crystal form I of hydrochloride | Crystal form I of hydrochloride |

Example 6: Preparation of Crystal Form I of a Sulfate Salt

Figure 9:
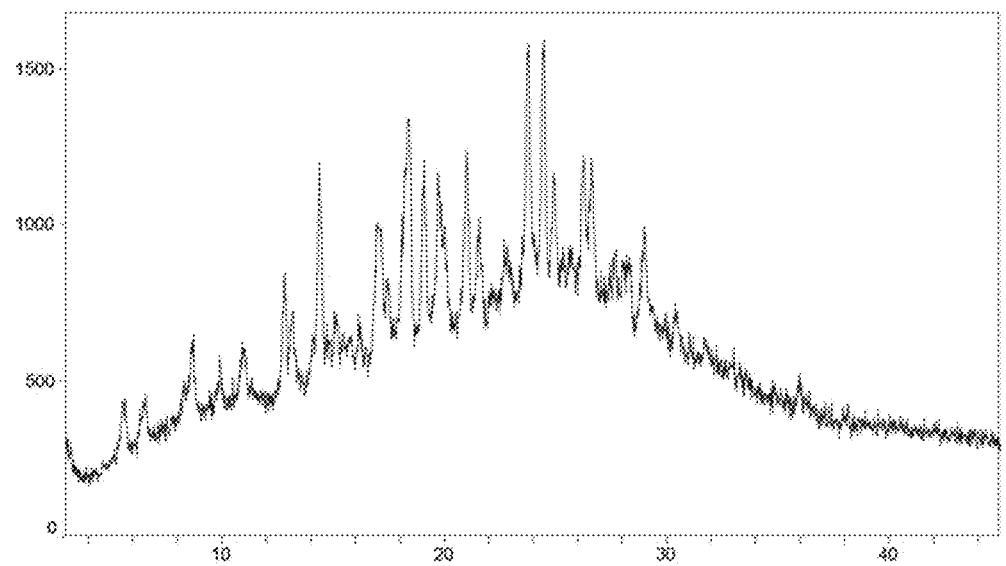
FIG. 9 is the X-ray powder diffraction spectrum of crystal form I of a sulfate salt of the compound of formula I; the abscissa is angle 2θ (°), and the ordinate is intensity.

About 20 mg of free base of the compound of formula I was weighed and placed in a 2 mL HPLC vial. Then, 1.0 mL of acetonitrile or acetone was added, and then 4.9 μL of 98% concentrated sulfuric acid solution were added. The mixture was magnetically stirred for about 2 days at room temperature and sufficiently crystallized to obtain crystal form I of the sulfate salt. Its X-ray powder diffraction spectrum is shown in FIG. 9.

| Initial state of the compound of formula I | Amorphous | Amorphous |
|---|---|---|
| Amount of the compound of formula I | 20 mg | 20 mg |
| Solvent name | Acetonitrile | Acetone |
| Solvent amount | 1 mL | 1 mL |
| Concentration | 20 mg/mL | 20 mg/mL |
| Concentrated sulfuric acid | 4.9 μL | 4.9 μL |
| Experimental temperature | Room temperature | Room temperature |
| Experimental results | Crystal form I of sulfate | Crystal form I of sulfate |

Example 7: Preparation of Crystal Form II of a Sulfate Salt

Figure 10:
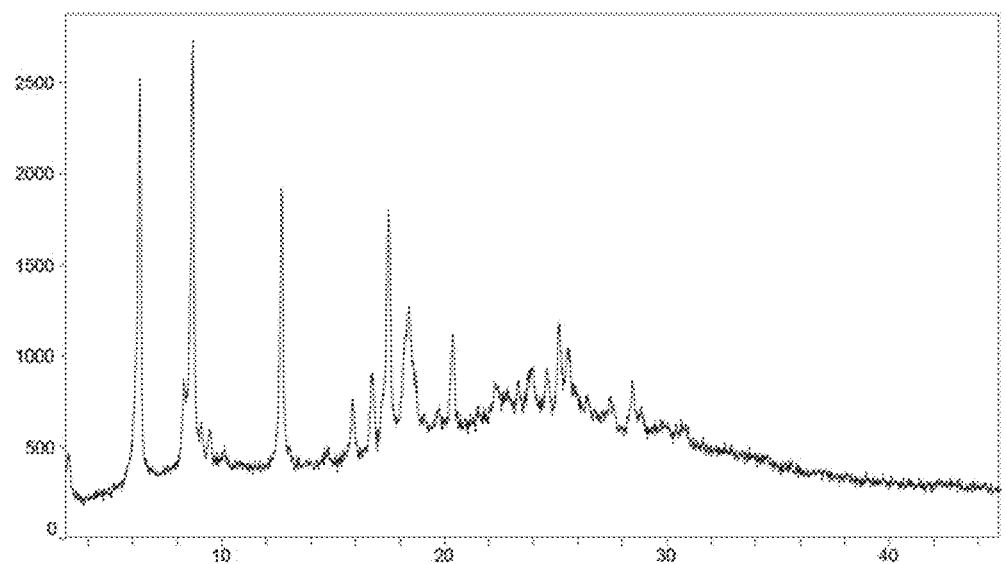
FIG. 10 is the X-ray powder diffraction spectrum of crystal form II of a sulfate salt of the compound of formula I; the abscissa is angle 2θ (°), and the ordinate is intensity.

About 20 mg of free base of the compound of formula I was weighed and placed in a 2 mL HPLC 1.0 mL of 50% ethanol was added, and then 4.9 μL of 98% concentrated sulfuric acid solution was added. The mixture was magnetically stirred about 2 days at room temperature and sufficiently crystallized to obtain crystal form II of sulfate, its X-ray powder diffraction spectrum was shown in FIG. 10.

Example 8: Preparation of Crystal Form I of a Phosphate Salt

Figure 11:
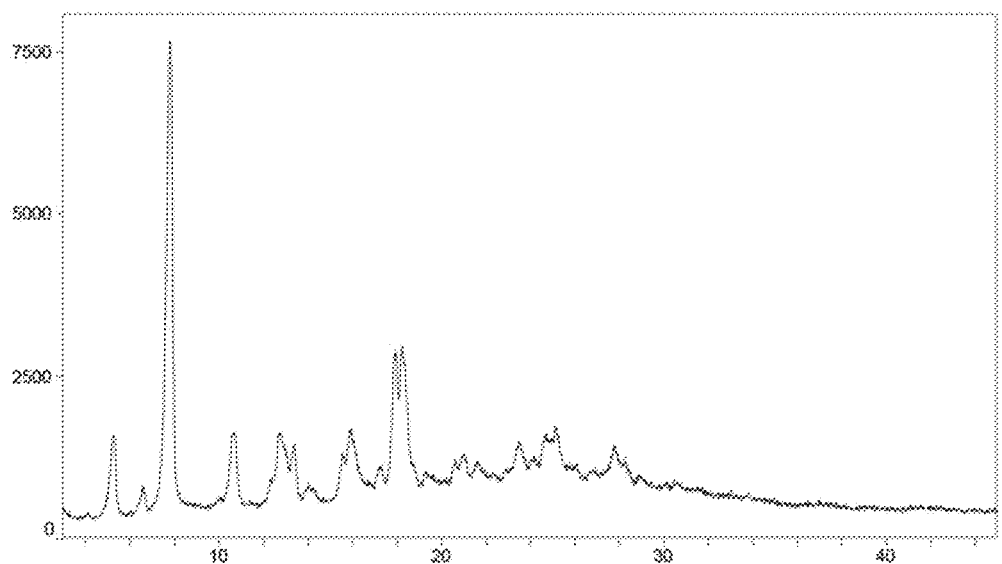
FIG. 11 is the X-ray powder diffraction spectrum of crystal form I of a phosphate salt of the compound of formula I; the abscissa is angle 2θ (°), and the ordinate is intensity.

About 20 mg of free base of the compound of formula I was weighed and placed in a 2 mL HPLC vial. Then, 1.0 mL of methanol or 50% ethanol was added, and then 7.5 μL of 85% phosphoric acid solution were added. The mixture was magnetically stirred for about 2 days at room temperature and sufficiently crystallized to obtain crystal form I of the phosphate salt. Its X-ray powder diffraction spectrum is shown in FIG. 11.

| Initial state of the compound of formula I | Amorphous | Amorphous |
|---|---|---|
| Amount of the compound of formula I | 20 mg | 20 mg |
| Solvent name | Methanol | 50% Ethanol/water |
| Solvent amount | 1 mL | 1 mL |
| Concentration | 20 mg/mL | 20 mg/mL |
| 85% phosphoric acid solution | 7.5 μL | 7.5 μL |

-continued

| | | |
|---|---|---|
| Experimental temperature | Room temperature | Room temperature |
| Experimental results | Crystal form I of phosphate | Crystal form I of phosphate |

Solubility of Crystal Form I of a Phosphate Salt in Different Simulated Biological Media Procedure: About 10 mg of crystal form I of a phosphate salt was weighed and placed in a 2 mL glass vial. Then, 1 mL of simulated biological media (simulated is artificial gastric juice, simulated artificial intestinal juice-fasting, and simulated artificial intestinal juice-satiety), and a magnetic stirrer were added, and then the vial was sealed. The mixture was magnetically stirred at 37° C. and about 0.4 mL of the sample was taken at different time points. The mixture was filtered with a centrifuge tube (pore size of filter membrane: 0.45 μm), the filtrate was taken and the content of the compound of formula I therein was analyzed by HPLC. Measurement results are shown in the table below:

| Crystal Form | Simulated biological media | Solubility (1 hour) mg/mL | Solubility (4 hours) mg/mL | Solubility (22 hours) mg/mL |
|---|---|---|---|---|
| Crystal form I of phosphate | Simulated artificial gastric juices | 0.128 | 0.135 | 0.135 |
| | Simulated artificial intestinal juice-fasting | 0.008 | 0.004 | 0.003 |
| | Simulated artificial intestinal juice-satiety | 0.032 | 0.033 | 0.027 |

The solubility of crystal form I of a phosphate salt, was much greater than the solubility of the free base, and the solubility of the compound of formula I was thus improved which is in favor of increasing the bioavailability.

Example 9: Preparation of Crystal Form II of a Phosphate Salt

Figure 12:
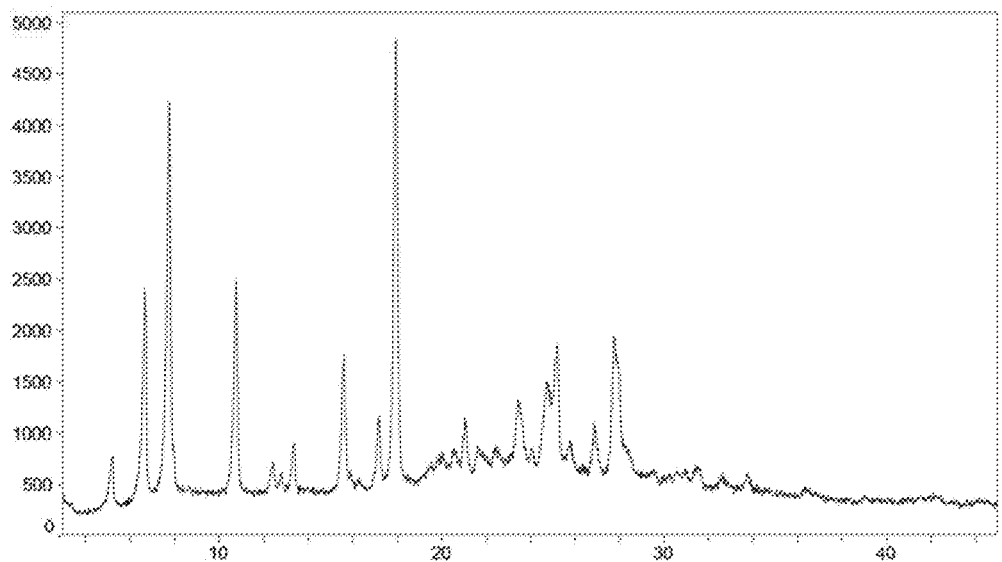
FIG. 12 is the X-ray powder diffraction spectrum of crystal form II of a phosphate salt, of the compound of formula I; the abscissa is angle 2θ (°), and the ordinate is intensity.

About 20 mg of free base of the compound of formula I was weighed and placed in a 2 mL HPLC vial. Then, 1.0 mL of acetonitrile, ethyl acetate or tetrahydrofuran was added, and then 7.5 μL of 85% phosphoric acid solution were added. The mixture was magnetically stirred for about 2 days at room temperature and sufficiently crystallized to obtain crystal form II of the phosphate salt. Its X-ray powder diffraction spectrum is shown in FIG. 12.

| | | | |
|---|---|---|---|
| Initial state of the compound of formula I | Amorphous | Amorphous | Amorphous |
| Amount of the compound of formula I | 20 mg | 20 mg | 20 mg |
| Solvent name | Acetonitrile | Ethyl acetate | Tetrahydrofuran |
| Solvent amount | 1 mL | 1 mL | 1 mL |
| Concentration | 20 mg/mL | 20 mg/mL | 20 mg/mL |
| 85% phosphoric acid solution | 7.5 μL | 7.5 μL | 7.5 μL |
| Experimental temperature | Room temperature | Room temperature | Room temperature |
| Experimental results | Crystal form II of phosphate | Crystal form II of phosphate | Crystal form II of phosphate |

Example 10: Preparation of Crystal Form III of a Phosphate Salt

Figure 13:
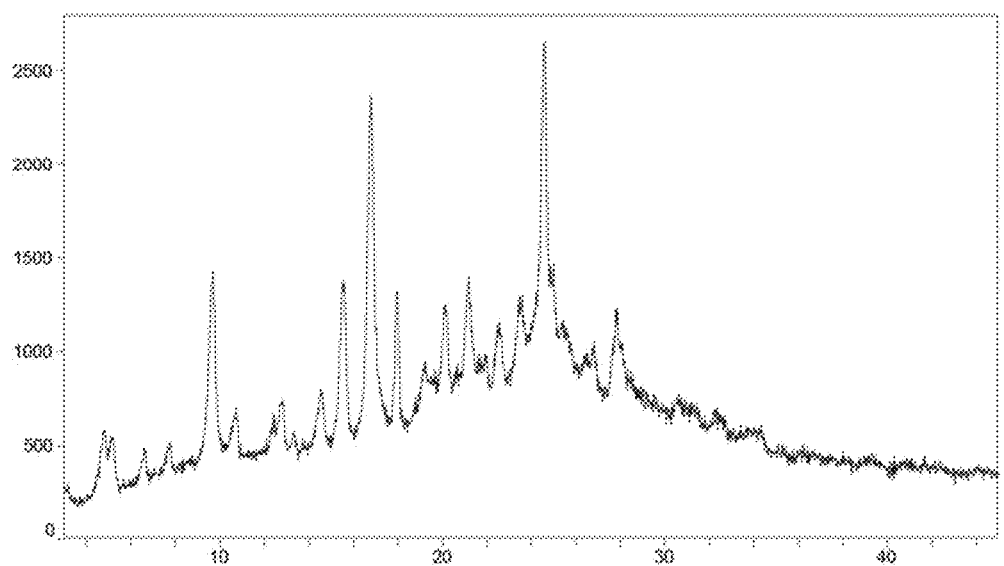
FIG. 13 is the X-ray powder diffraction spectrum of crystal form III of a phosphate salt of the compound of formula I; the abscissa is angle 2θ (°), and the ordinate is intensity.

About 20 mg of free base of the compound of formula I was weighed and placed in a 2 mL HFLC vial. Then, 1.0 mL of acetone was added, and then 7.5 μL of 85% phosphoric acid solution were added. The mixture was magnetically stirred for about 2 days at room temperature and sufficiently crystal to obtain crystal form III of the phosphate salt, its X-ray powder diffraction spectrum is shown in FIG. 13.

Example 11: Preparation of Crystal Form IV of a Phosphate Salt

Figure 14:
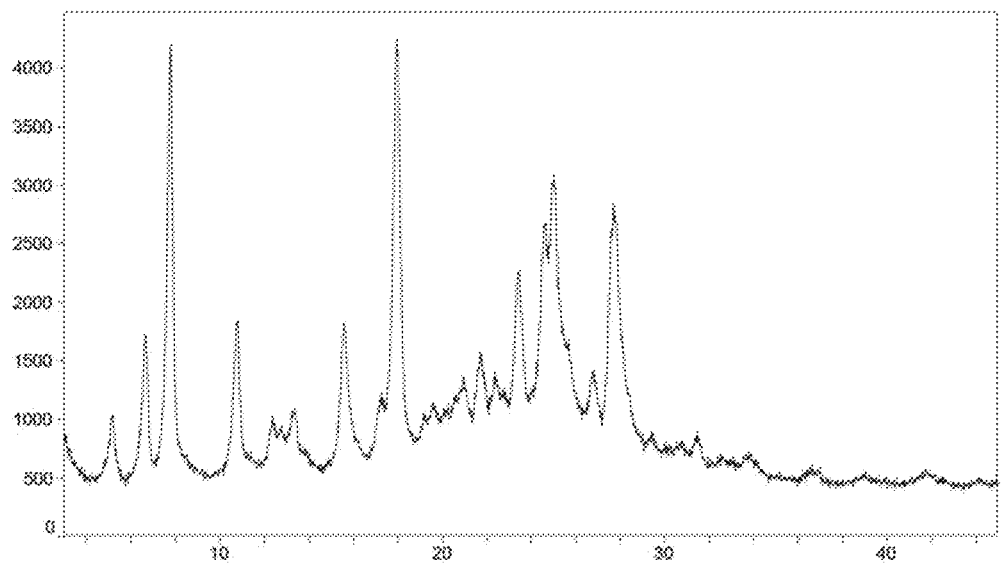
FIG. 14 is the X-ray powder diffraction spectrum of crystal form IV of a phosphate salt of the compound of formula I; the abscissa is angle 2θ (°), and the ordinate is intensity.

About 20 mg of free base of the compound of formula I was weighed and placed in a 2 mL HPLC vial. Then, 5.0 mL of methanol was added, and then 37.5 μL of 85% phosphoric acid solution were added. The mixture was magnetically stirred for about 2 days at room temperature and sufficiently crystallized to obtain crystal form IV of the phosphate salt. Its X-ray powder diffraction spectrum is shown m FIG. 14.

Example 12: Preparation of Crystal Form I of a Mesylate Salt

Figure 15:
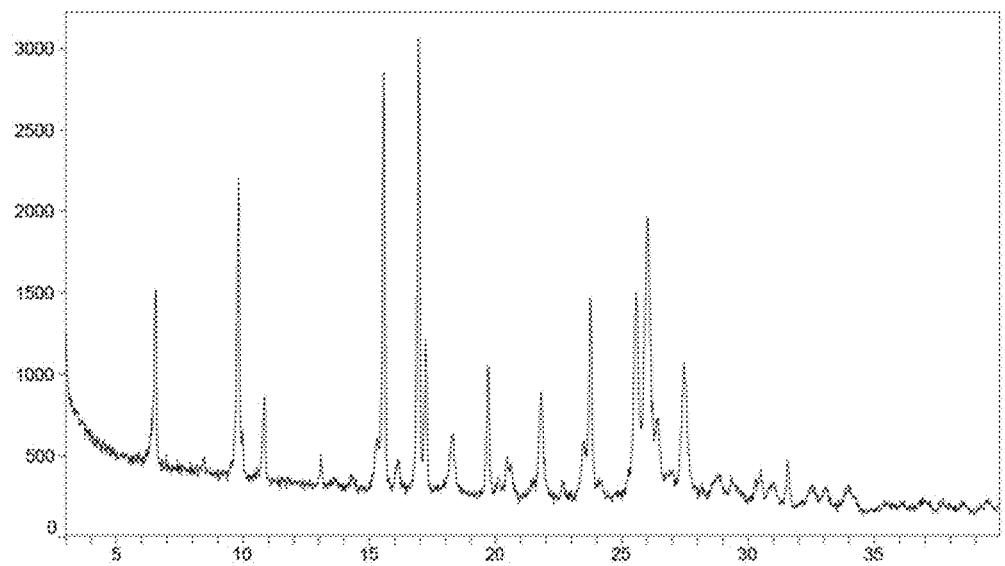
FIG. 15 is the X-ray powder diffraction spectrum of crystal form I of a mesylate salt of the compound of formula I; the abscissa is angle 2θ (°), and the ordinate is intensity.

A certain amount of free base of the compound of formula I was weighed and placed in a container. A suitable solvent was added, then an equal or excess molar equivalent of methanesulfonic acid was added. The mixture was stirred, and after the salt-forming reaction was completed, a solid-liquid separation was carried out to obtain crystal form I of the mesylate (hydrate) salt. Its X-ray powder diffraction spectrum is shown in FIG. 15. For example:

About 20 mg of free base of the compound of formula I was weighed and placed in a 2 mL HPLC vial. Then, 1.0 mL of acetone was added, and then 6.2 μL of 98% methanesulfonic acid solution was added. The mixture was magnetically stirred for about 2 days at room temperature and sufficiently crystallized to obtain crystal form I of the mesylate salt.

| | | | | | | |
|---|---|---|---|---|---|---|
| Initial state of the compound of formula I | Free base | Free base | Free base | Free base | Free base | Free base |
| Amount of compound I | 20 mg | 20 mg | 20 mg | 20 mg | 20 mg | 20 mg |
| Solvent name | Acetone | Ethyl acetate | Tetrahydrofuran | Isopropyl acetate | 2-Methoxy ethyl ether | 1,4-Dioxane |

| | | | | | | |
|---|---|---|---|---|---|---|
| Solvent amount | 1 mL | 1 mL | 1 mL | 1 mL | 1 mL | 1 mL |
| Concentration | 20 mg/mL | 20 mg/mL | 20 mg/mL | 20 mg/mL | 20 mg/mL | 20 mg/mL |
| 98% methanesulfonic acid | 6.2 μL | 6.2 μL | 6.2 μL | 6.2 μL | 6.2 μL | 6.2 μL |
| Experimental temperature | Room temperature | Room temperature | Room temperature | Room temperature | Room temperature | Room temperature |
| Experimental results | Crystal form I of mesylate | Crystal form I of mesylate | Crystal form I of mesylate | Crystal form I of mesylate | Crystal form I of mesylate | Crystal form I of mesylate |

Example 13: Preparation of Crystal Form II of the Mesylate Salt

Figure 16:
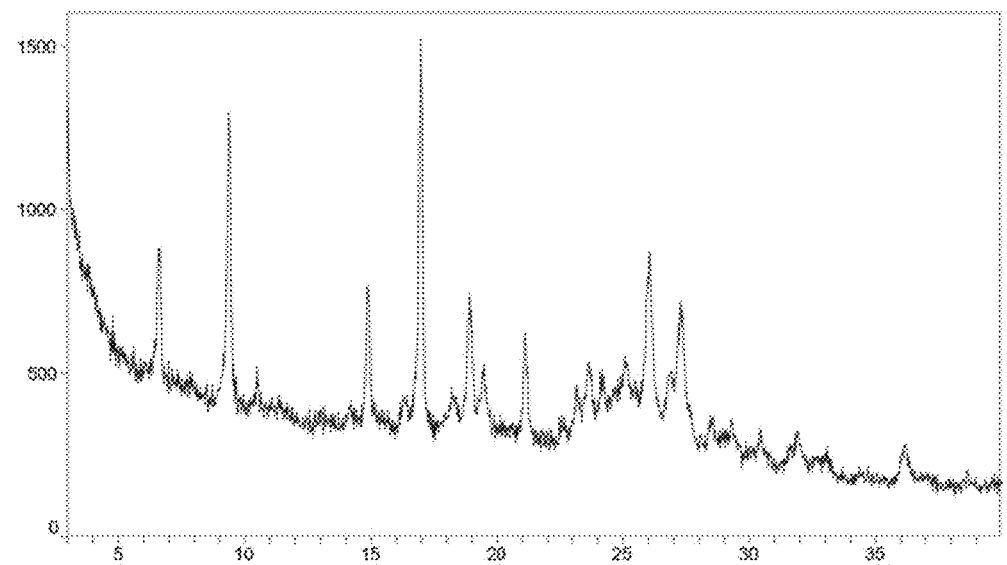
FIG. 16 is the X-ray powder diffraction spectrum of crystal form II of a mesylate salt of the compound of formula I; the abscissa is angle 2θ (°), and the ordinate is intensity.

A certain amount of free base of the compound of formula I was weighed and placed in a container. A mixed solvent of methanol and water (methanol/water volume ratio of 5%-95%) was added. The mixture was stirred, and then an equal or excess molar equivalent of methanesulfonic acid was added until the solution became clear. After mesylate was precipitated, a solid-liquid separation was carried out to obtain crystal form II of the mesylate (hydrate) salt, Its X-ray powder diffraction spectrum is shown in FIG. 16.

Example 14: Preparation of Crystal Form III of a Mesylate Salt

Figure 17:
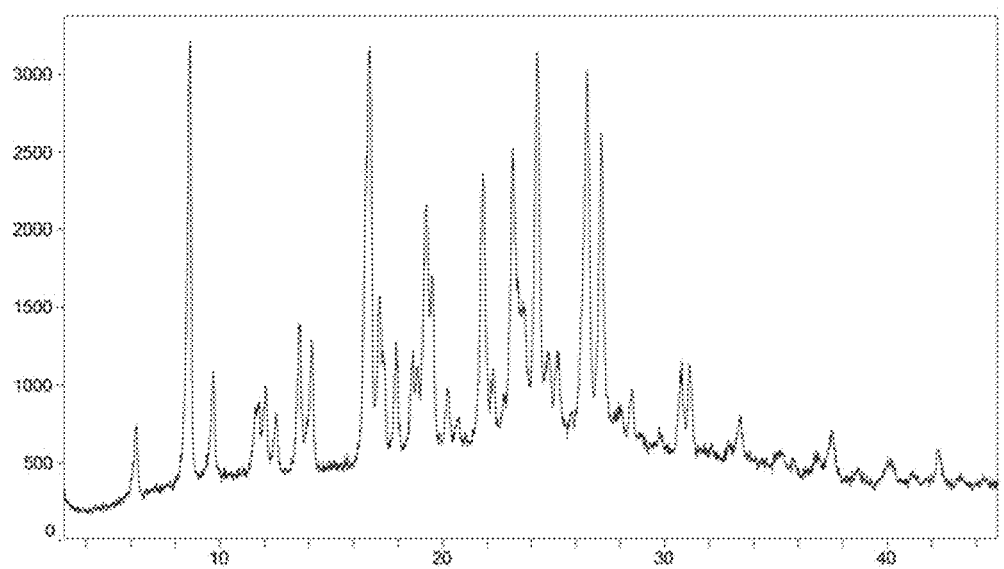
FIG. 17 is the X-ray powder diffraction spectrum of crystal form III of a mesylate salt of the compound of formula I; the abscissa is angle 2θ (°), and the ordinate is intensity.

Method 1:

About 20 mg of free base of the compound of formula I was weighed and placed in a 2 mL HPLC vial. Then, 1.0 mL methanol was added, and then 6.2 μL of 98% methanesulfonic acid were added. The mixture was magnetically stirred for about 2 days at room temperature and sufficiently crystallized to obtain mesylate, and then dried for 1 day in a vacuum oven at 100° C. to obtain crystal form III of the mesylate salt. Its X-ray powder diffraction spectrum is shown in FIG. 17.

Method 2:

Crystal form IV of the mesylate salt was dried in a vacuum overnight. Crystal form IV of the mesylate salt was transformed into crystal form III of the mesylate salt. Its X-ray powder diffraction spectrum was consistent with FIG. 17.

Method 3:

About 300 mg of crystal form V of the mesylate salt was weighed and placed in a 20 mL glass vial. Then, 15 of 25% ethyl acetate/n-heptane (v/v) solution was added. The mixture was stirred for 24 hours at 40° C., and then was filtered to obtain crystal form III of the mesylate salt. Its X-ray powder diffraction spectrum was consistent with FIG. 17.

Figure 18:
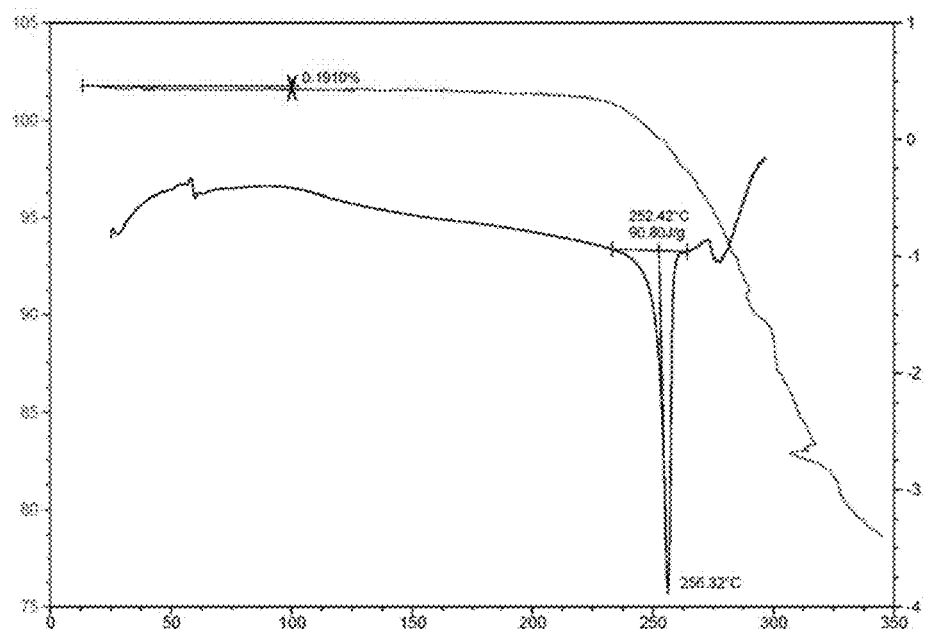
FIG. 18 is the DSC/TGA stacking spectrum of crystal form III of a mesylate salt of the compound of formula I; the abscissa is temperature (° C.), the right ordinate is heat flow (W/g), and the exothermic peak is upward; and the left ordinate is weightlessness ratio (%)

The melting point of crystal form III of the mesylate salt was measured by differential scanning calorimetry (DSC, model: TA Q2000). Measurement conditions: heating from room temperature to 300° C. at a heating rate of 10° C. per minute in a nitrogen atmosphere and a nitrogen flow rate of 20 mL per minute. The DSC spectrum of crystal form III of mesylate is shown in FIG. 18. The melting point of crystal form III of the mesylate salt (onset temperature) was 252.4° C. The thermal weightlessness of crystal form III of the mesylate salt was measured by a thermal gravimetric analyzer (TGA, model: TA Q500). Measurement conditions: heating from room temperature to 350° C. at a heating rate of 10° C. per minute in a nitrogen atmosphere and a nitrogen flow rate of 50 mL per minute. The TGA spectrum of crystal form III of the mesylate salt is shown in FIG. 18. Due to almost no weight loss below 100° C., it was determined that crystal form III of the mesylate salt is an anhydrous compound.

Solubility of Crystal Form III of the Mesylate Salt in Different Simulated Biological Media Procedure: About 10 mg of crystal form III of the mesylate salt was weighed and placed in a 2 mL glass vial. Then, 1 mL of simulated biological media (simulated artificial gastric juice, simulated artificial intestinal juice-fasting, and simulated artificial intestinal juice-satiety), and a magnetic stirrer were added, and then the vial was sealed. The mixture was magnetically stirred at 37° C. and about 0.4 mL of the sample was taken at different time points. The mixture was filtered with a centrifuge tube (pore size of filter membrane: 0.45 μm), the filtrate was taken and the content of the compound of formula I therein was analyzed by HPLC. Measurement results are shown in the table below:

| Crystal Form | Simulated biological media | Solubility (1 hour) mg/mL | Solubility (4 hours) mg/mL | Solubility (22 hours) mg/mL |
|---|---|---|---|---|
| Crystal form III of mesylate | Simulated artificial gastric juices | 0.211 | 0.200 | 0.0125 |
| | Simulated artificial intestinal juice-fasting | 0.005 | 0.005 | 0.005 |
| | Simulated artificial intestinal juice-satiety | 0.020 | 0.014 | 0.010 |

The solubility of crystal form III of the mesylate salt was much greater than the solubility of the free base, and the solubility of the compound of formula I was thus improved which is in favor of increasing the bioavailability.

The accelerated stability test of crystal form III of the mesylate salt was used for researching the physical and chemical stability of crystal form III of the mesylate salt. Specific procedure: After the sample was placed in an accelerated stability for a sufficient time under the conditions shown in the table below, the sample was taken out and dissolved in the mobile phase, and then its purity was determined by HPLC. Before the start of the accelerated stability test, the purity of the initial sample was determined by HPLC. The ratio of the purity of the sample after the accelerated stability test to the purity of the initial sample was used as a stability criterion. If the ratio was less than 95% purity, the sample was considered as unstable. Specific experimental conditions and results are shown in the table below:

| Crystal Form | Accelerated test condition | Period | Initial purity | Purity after the accelerated stability test | Purity ratio | Crystal transformation after the accelerated stability test |
| --- | --- | --- | --- | --- | --- | --- |
| Crystal form III of mesylate | 80° C. | 1 day | 99.9% | 99.7% | 99.8% | No transformation |
| | 40° C./75% relative humidity | 1 week | 98.2% | 98.8% | 100.6% | No transformation |

From the results in the above table, it could be seen that crystal form III of the mesylate salt has good physical and chemical stability under the above conditions.

Figure 21:
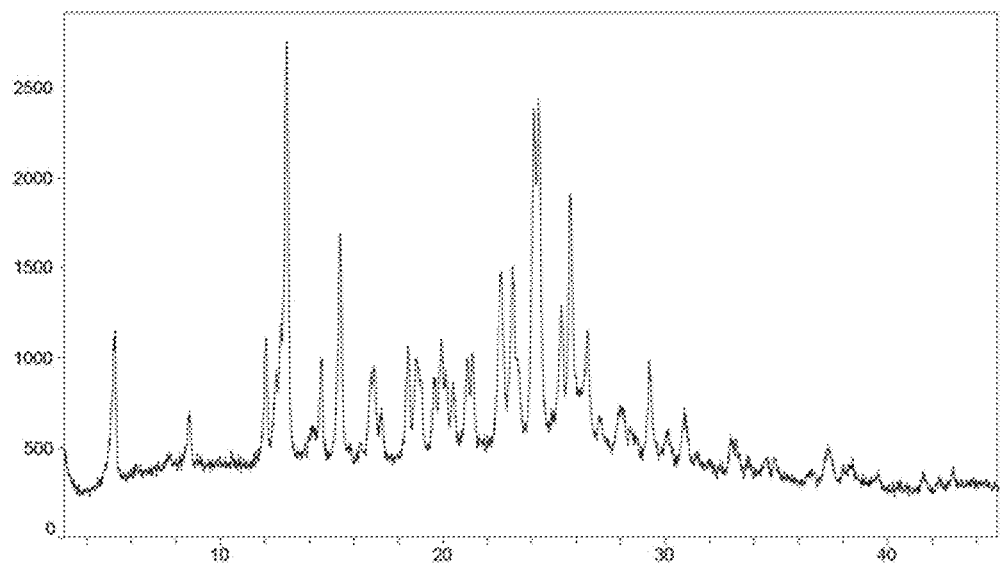
FIG. 21 is the X-ray powder diffraction spectrum of crystal form I of a p-toluenesulfonate salt of the compound of formula I; the abscissa is angle 2θ (°), and the ordinate is intensity.
Figure 22:
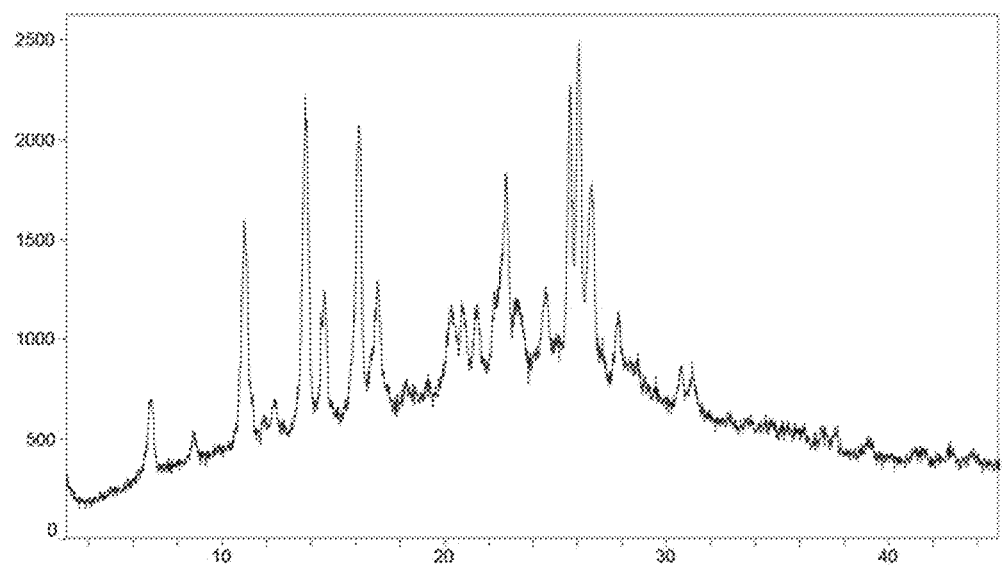
FIG. 22 is the X-ray powder diffraction spectrum of crystal form II of a p-toluenesulfonate salt of the compound of formula I; the abscissa is angle 2θ (°), and the ordinate is intensity.
Figure 23:
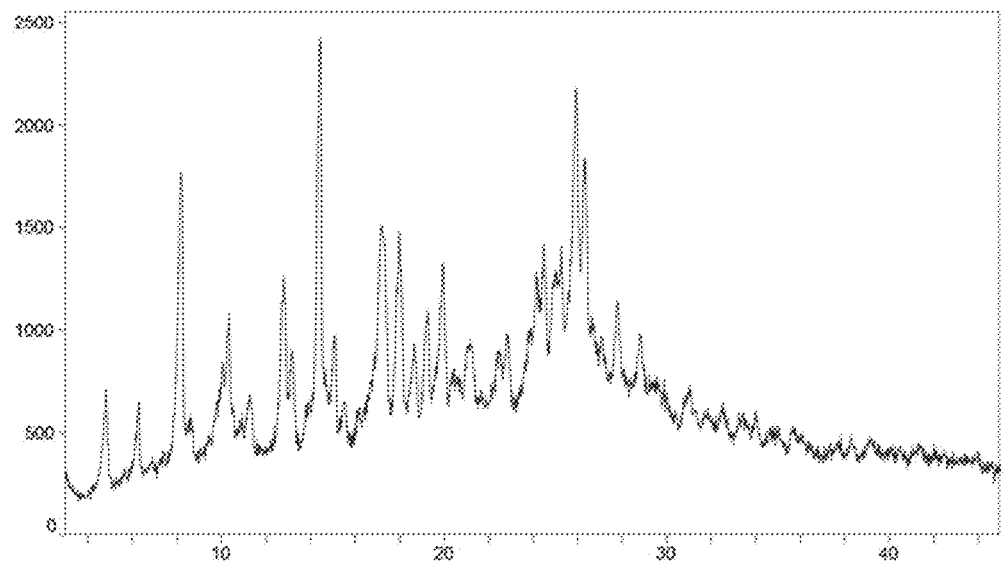
FIG. 23 is the X-ray powder diffraction spectrum of crystal form III of a p-toluenesulfonate salt of the compound of formula I; the abscissa is angle 2θ (°), and the ordinate is intensity.
Figure 24:
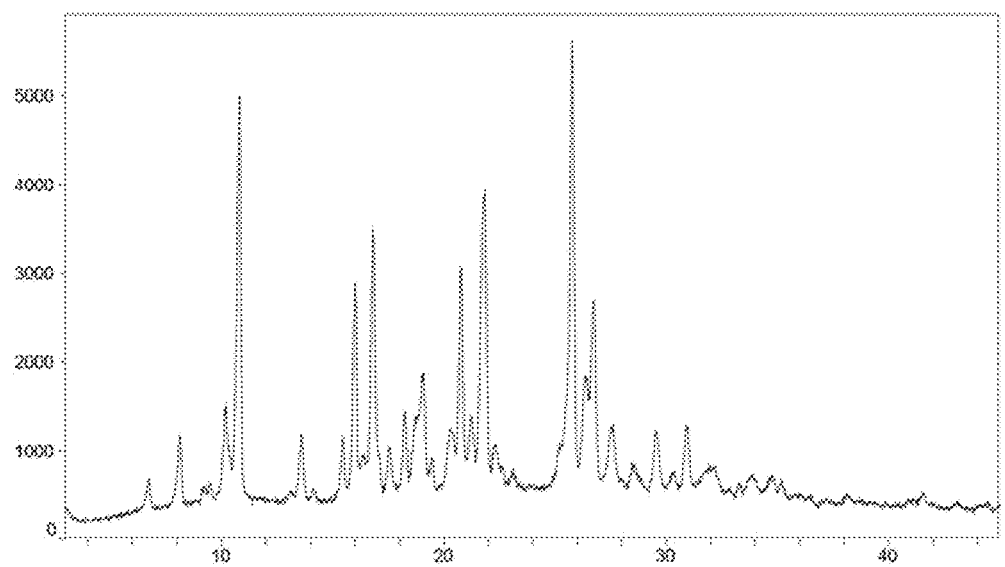
FIG. 24 is the X-ray powder diffraction spectrum of crystal form I of a 1,5-naphthalenedisulfonate salt of the compound of formula I; the abscissa is angle 2θ (°), and the ordinate is intensity.

It could be seen from FIG. 21 that the bioavailability of crystal form III of the mesylate salt was increased by 5 times in comparison to form I of the free base. Experimental conditions: the experimental animal was a dog, a dose of 5 mg/kg, single administration by gavage. Therefore, the salt-form compound has a significant improvement in comparison to the free base.

Example 15: Preparation of Crystal Form IV of a Mesylate Salt

Figure 19:
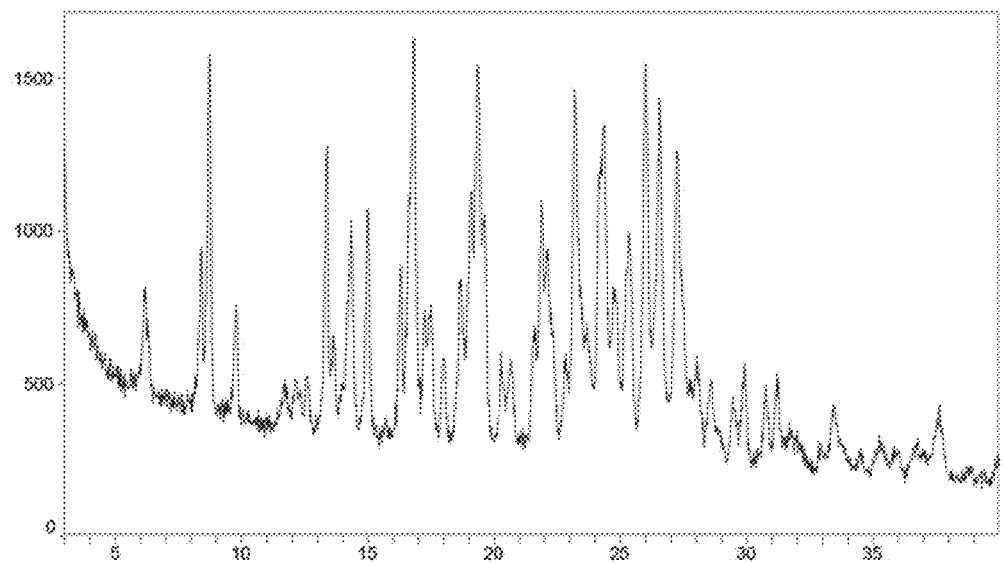
FIG. 19 is the X-ray powder diffraction spectrum of crystal form IV of a mesylate salt of the compound of formula I; the abscissa is angle 2θ (°), and the ordinate is intensity.

About 20 mg of free base of the compound of formula I was weighed and placed in a 2 mL HPLC vial. Then, 1.0 of methanol was added, and then 6.2 μL of 98% methanesulfonic acid solution were added. The mixture was magnetically stirred for about 2 days at room temperature and sufficiently crystallized to obtain crystal form IV of the mesylate salt. Its X-ray powder diffraction spectrum is shown in FIG. 19.

Example 16: Preparation of Crystal Form V of a Mesylate Salt

Figure 20:
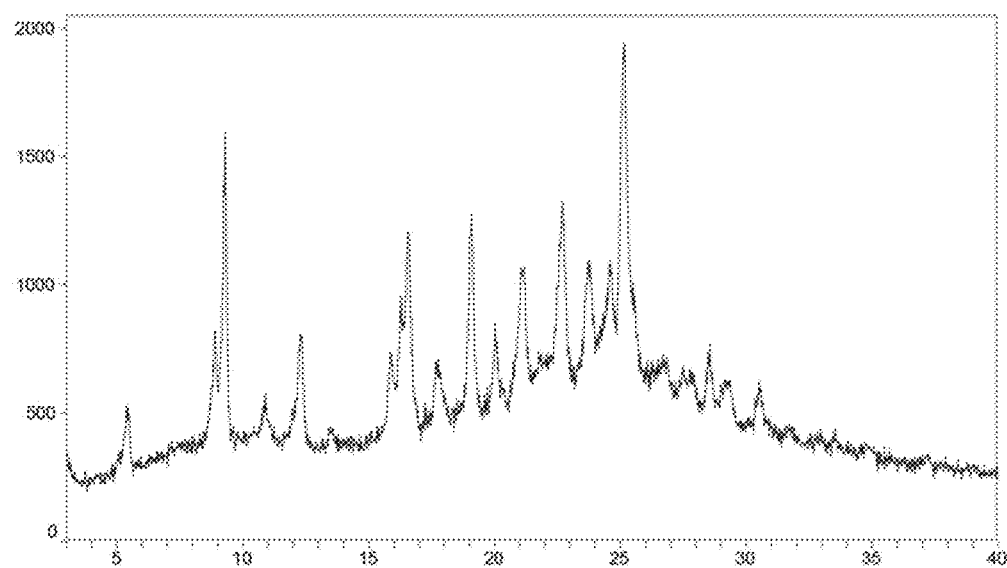
FIG. 20 is the X-ray powder diffraction spectrum of crystal form V of a mesylate salt of the compound of formula I; the abscissa is angle 2θ (°), and the ordinate is intensity.

About 100 mg of free base of the compound of formula I was weighed and placed in a 10 mL glass vial. Then, 2.0 mL of DMSO were added, and then 31.2 μL of 98% methanesulfonic acid solution were added. The mixture was stirred at room temperature until the solution was clear. The mixture was filtered, and then 3 mL of ethyl acetate was add to the filtrate. After stirring for 24 hours, the mixture was filtered to obtain crystal form V of the mesylate salt (DMSO solvate). Its X-ray powder diffraction spectrum is shown in FIG. 20.

The formation of crystal form V of the mesylate salt (DMSO solvate) played a role in purifying and refining of the compound of formula I.

| Crystal Form | Purity |
| --- | --- |
| Free base of formula I | 95.0% |
| DMSO solvate of mesylate | 99.7% |

In addition, the formation of crystal form V of the mesylate salt brings great convenience in the unit operation, because the compound of formula I can be dissolved in DMSO, it is easy to achieve on-line filtration, and the solution is transported to the GMP workshop through a pipeline. Then, the compound of formula I is reacted with methanesulfonic acid, and the resulting product is precipitated from the solution, then crystal form V of the mesylate salt is obtained by filtration, thereby purifying the compound of formula I. As an important product of this advanced purification method, crystal form V has valuable practical application.

Example 17: Preparation of Crystal Form I of a p-Toluenesulfonate Salt

About 20 mg of free base of the compound of formula I was weighed and placed in a 2 mL HPLC vial. Then, 1.0 mL of methanol was added, and then 8.6 μL of 98% p-toluenesulfonic acid solution were added. The mixture was magnetically stirred for about 2 days at room temperature and sufficiently crystallized to obtain crystal form I of p-toluenesulfonate. Its X-ray powder diffraction spectrum data are shown in Table 17 above.

| Initial state of the compound of formula I | Free base | Free base | Free base |
| --- | --- | --- | --- |
| Amount of the compound of formula I | 20 mg | 20 mg | 20 mg |
| Solvent name | Methanol | Acetonitrile | Acetone |
| Solvent amount | 1 mL | 1 mL | 1 mL |
| Concentration | 20 mg/mL | 20 mg/mL | 20 mg/mL |
| 98% p-toluenesulfonic acid | 8.6 μL | 8.6 μL | 8.6 μL |
| Experimental temperature | Room temperature | Room temperature | Room temperature |
| Experimental results | Crystal form I of p-toluenesulfonate | Crystal form I of p-toluenesulfonate | Crystal form I of p-toluenesulfonate |

Example 18: Preparation of Crystal Form II of a p-Toluenesulfonate Salt

About 20 tug of free base of the compound of formula I was weighed and placed in a 2 mL HPLC vial. Then, 1.0 mL of ethyl acetate was added, and then 8.6 μL of 98% p-toluenesulfonic acid solution were added. The mixture was magnetically stirred for about 2 days at room temperature and sufficiently crystallized to obtain crystal form II of the p-toluenesulfonate salt. Its X-ray powder diffraction spectrum data are shown in Table 18 above.

Example 19: Preparation of Crystal Form III or a p-toluenesulfonate Salt

About 20 in of free base of the compound of formula I was weighed and placed in a 2 mL HPLC vial. Then, 1.0 mL of 50% methanol was added, and then 8.6 μL of 98% p-toluenesulfonic acid solution were added. The mixture was magnetically stirred for about 2 days at room temperature and sufficiently crystallized to obtain crystal form III of the p-toluenesulfonate salt. Its X-ray powder diffraction spectrum data are shown in Table 19 above.

Example 20: Preparation of Crystal Form I of a 1,5-naphthalenedisulfonate Salt A certain amount of free base of the compound of formula I was weighed and placed in a container. Methanol, acetonitrile or acetone was added, and then an equal or excess molar equivalent of 1,5-naphthalenedisulfonic acid was added. The mixture was stirred, and after the salt-forming reaction was completed, a solid-liquid separation was carried out to obtain crystal form I of the 1,5-naphthalenedisulfonate salt.

About 20 mg of free base of the compound of formula I was weighed and placed in a 2 mL HPLC vial. Then, 1.0 mL of acetone was added, and then 23.8 mg of 1,5-naphthalenedisulfonic acid was added. The mixture was magnetically stirred for about 2 days at room temperature and sufficiently crystallized to obtain crystal form I of the 1,5-naphthalenedisulfonate salt. Its X-ray powder diffraction spectrum data are shown in Table 20 above.

| Initial state of the compound of formula I | Free base | Free base | Free base |
| --- | --- | --- | --- |
| Amount of the compound of formula I | 20 mg | 20 mg | 20 mg |
| Solvent name | Methanol | Acetonitrile | Acetone |
| Solvent amount | 1 mL | 1 mL | 1 mL |
| Concentration | 20 mg/mL | 20 mg/mL | 20 mg/mL |
| 2-Naphthalenesulfonic acid | 23.8 mg | 23.8 mg | 23.8 mg |
| Experimental temperature | Room temperature | Room temperature | Room temperature |
| Experimental results | Crystal form I of 1,5-naphthalenedisulfonate | Crystal form I of 1,5-naphthalenedisulfonate | Crystal form I of 1,5-naphthalenedisulfonate |

Figure 25:
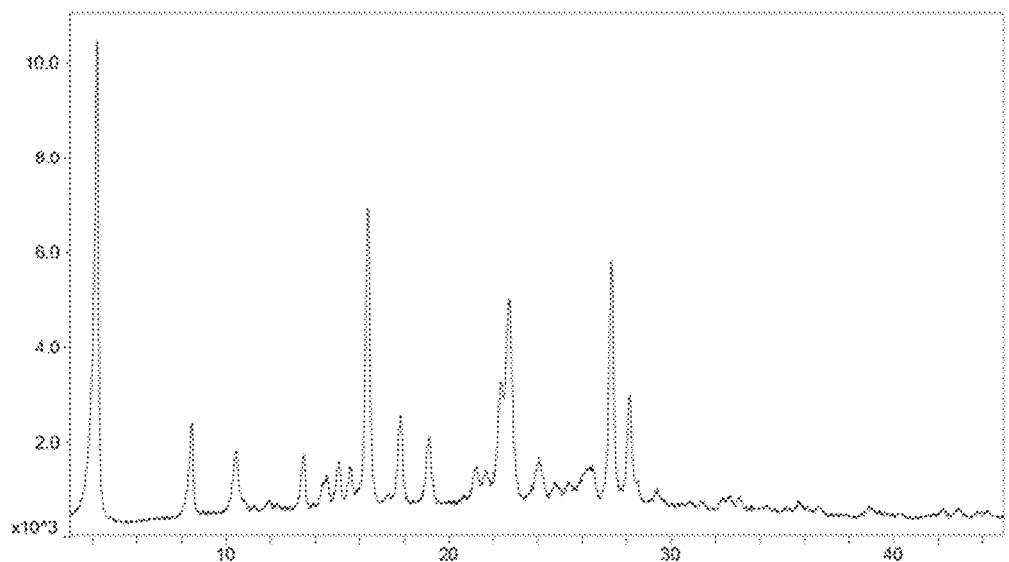
FIG. 25 is the X-ray powder diffraction spectrum of crystal form II of a 1,5-naphthalenedisulfonate salt of the compound of formula I; the abscissa is angle 2θ (°), and the ordinate is intensity.

Example 21: Preparation of Crystal Form II of a 1,5-Naphthalenedisulfonate Salt About 20 mg of free base of the compound of formula I was weighed and placed in a 2 mL HPLC vial. Then, 1.0 mL of ethyl acetate was added, and then 23.8 mg 1,5-naphthalenedisulfonic acid were added. The mixture was magnetically stirred for about 2 days at room temperature and sufficiently crystallized to obtain crystal form II of the 1,5-naphthalenedisulfonate salt. Its X-ray powder diffraction spectrum is shown in FIG. 25.

Figure 26:
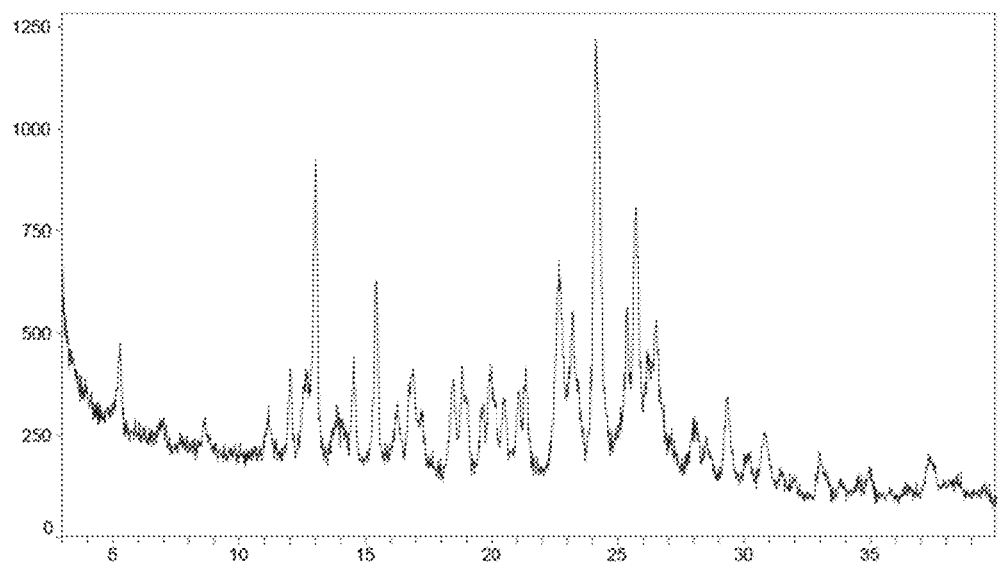
FIG. 26 is the X-ray powder diffraction spectrum of crystal form III of a 1,5-naphthalenedisulfonate salt of the compound of formula I; the abscissa is angle 2θ (°), and the ordinate is intensity.

Example 22: Preparation of Crystal Form III of a 1,5-Naphthalenedisulfonate Salt About 100 mg of free base of the compound of formula I was weighed and placed in a 20 mL HPLC vial. Then, 5.0 mL of methanol were added, and then 119 mg of 1,5-naphthalenedisulfonic acid were added. The mixture was magnetically stirred for about 2 days at room temperature and sufficiently crystallized to obtain crystal form III of the 1,5-naphthalenedisulfonate salt. Its X-ray powder diffraction spectrum is shown in FIG. 26.

Figure 27:
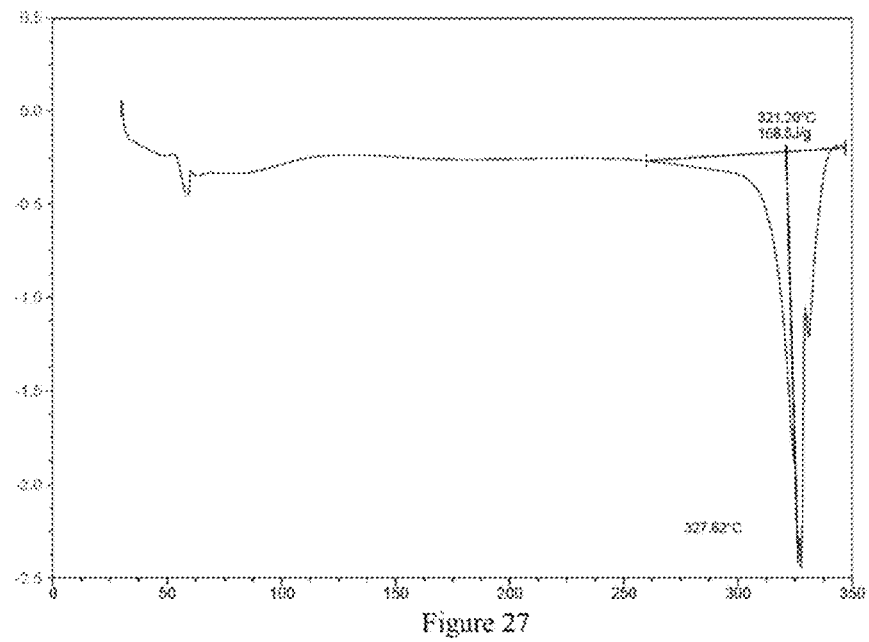
FIG. 27 is the DSC spectrum of crystal form III of a 1,5-naphthalenedisulfonate salt of the compound of formula I; the abscissa is temperature (° C.), and the ordinate is heat flow (W/g); the exothermic peak is upward.
Figure 28:
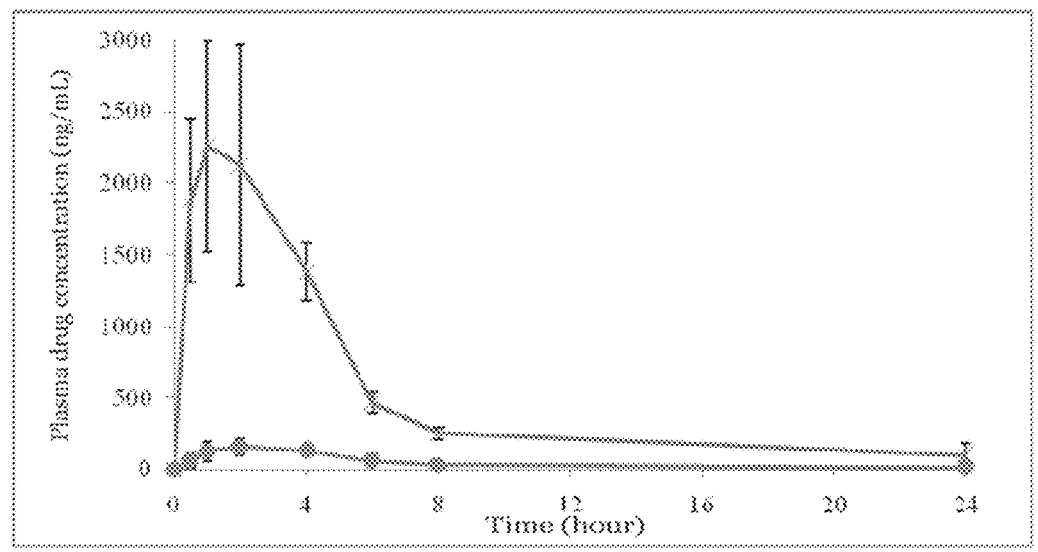
FIG. 28 is the plasma drug concentration-time curve of crystal form of a mesylate salt and crystal form I of the free base of the compound of formula I.

The melting point of crystal form III of the 1,5-naphthalenedisulfonate salt was measured by differential scanning calorimetry (DSC, model: TA Q2000). Measurement conditions: heating from room temperature to 300° C. at a heating rate of 10° C. per minute in a nitrogen atmosphere, and a nitrogen flow rat of 20 mL per minute. The DSC spectrum of crystal form III of the 1,5-naphthalenedisulfonate salt is shown in FIG. 27. The melting point of crystal form III of the 1,5-naphthalenedisulfonate salt (onset temperature) was 321.2° C.

Solubility of Crystal Form III of the 1,5-naphthalenedisulfonate Salt in Different Simulated Biological Media Procedure: About 10 mg of crystal form III of the 1,5-naphthalenedisulfonate salt was weighed and placed in a 2 mL glass vial. Then, 1 mL of simulated biological media (simulated artificial gastric juice, simulated artificial intestinal juice-fasting, and simulated artificial intestinal juice-satiety), and a magnetic stirrer were added, and then the vial was sealed. The mixture was magnetically stirred at 37° C. and about 0.4 mL of the sample was taken at different time points. The mixture was filtered with a centrifuge tube (pore size of filter membrane: 0.45 μm), the filtrate was taken and the content of the compound of formula I therein was analyzed by HPLC. Measurement results are shown in the table below:

| Crystal form | Simulated biological media | Solubility (1 hour) mg/mL | Solubility (4 hours) mg/mL | Solubility (22 hours) mg/mL |
| --- | --- | --- | --- | --- |
| Crystal form III of the 1,5-naphthalenedisulfonate salt | Simulated artificial gastric juices | 0.182 | 0.027 | 0.030 |
| | Simulated artificial intestinal juice-fasting | 0.012 | 0.010 | 0.005 |
| | Simulated artificial intestinal juice-satiety | 0.048 | 0.033 | 0.013 |

The solubility of crystal form III of the 1,5-naphthalenedisulfonate salt was much greater than the solubility of the free base, and the solubility of the compound of formula I was thus improved which is in favor of increasing the bioavailability. Finally, it should be noted that the above examples are used only to illustrate the technical solution of the present invention, but are not used to limit the scope of the present invention. Although the present invention has been described in detail with reference to the preferred examples, those skilled in the field will understand that the technical solution of the present invention can be modified or equivalently varied without departing from the spirit and scope of the invention, and such modifications and variations should be included in the claims of the present invention.

What is claimed is:

1. A crystalline acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3 (4H)-one, wherein the crystalline acid salt is an inorganic acid salt or an organic acid salt; wherein the inorganic acid salt is phosphate; and wherein the organic acid salt is selected from the group consisting of mesylate and 1,5-naphthalenedisulfonate;

wherein:
the phosphate salt is crystal form I of a phosphate salt, wherein crystal form I of the phosphate salt has an X-ray powder diffraction (XRPD) spectrum comprising peaks at diffraction angles (2θ) of 7.9±0.20, 12.8±0.2°, 15.9±0.2° and 18.3±0.2°;

the mesylate salt is crystal form III of a mesylate salt, wherein crystal form III of the mesylate salt has an XRPD spectrum comprising peaks at diffraction angles (2θ) of 16.7±0.20, 19.3±0.2°, 23.2±0.2° and 26.5±0.2°;

the 1,5-naphthalenedisulfonate salt is crystal form III of a 1,5-naphthalenedisulfonate salt wherein crystal form III of the the 1,5-naphthalenedisulfonate salt has an XRPD spectrum comprising peaks at diffraction angles (2θ) of 13.0±0.2°, 22.7±0.20, 24.1±0.20 and 25.7±0.20.

2. The crystalline acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one according to claim 1, wherein the acid salt is crystal form I of a phosphate salt,
wherein crystal form I of the phosphate salt has an X-ray powder diffraction (XRPD) spectrum comprising peaks at diffraction angles (2θ) of 7.9±0.20, 12.8±0.2°, 15.9±0.2° and 18.3±0.2°.

3. The crystalline acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one according to claim 1, wherein the acid salt is a crystal form III of a mesylate salt,
wherein crystal form III of the mesylate salt has an XRPD spectrum comprising peaks at diffraction angles (2θ) of 16.7±0.20, 19.3±0.2°, 23.2±0.2° and 26.5±0.2°.

4. The crystalline acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one according to claim 1, wherein the acid salt is crystal form III of a 1,5-naphthalenedisulfonate salt,
wherein crystal form III of the 1,5-naphthalenedisulfonate salt has an XRPD spectrum comprising peaks at diffraction angles (2θ) of 13.0±0.2°, 22.7±0.20, 24.1±0.2° and 25.7±0.2°.

5. A method for preparing a crystalline acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one according to claim 1, comprising the following steps of:
(1) a salt-forming process comprising dissolving or dispersing a free base of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one in an aqueous solvent or an organic solvent to obtain a salt-forming system, then adding a liquid or solid inorganic acid or organic acid or a solution of inorganic acid or organic acid to the salt-forming system to obtain an acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one; or
a salt-forming process comprising adding a free base solid of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one to an acid solution to obtain an acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one;
(2) collecting a solid product precipitated during the salt-forming process, or obtaining a solid product by creating supersaturation of the salt-forming system to prepare the crystalline acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one, wherein a method for creating supersaturation of the salt-forming system comprises evaporation of solvent, addition of an anti-solvent, or a cooling method;
and optionally
transforming a first crystal form of the acid salt into a second crystal form of the acid salt by a crystal transformation method, wherein the crystal transformation method comprises heating or a crystal transformation method via a mixed suspension in a suitable solvent;
wherein the organic solvent of the salt-forming process in step (1) is selected from the group consisting of alcohols, chloralkanes, ketones, ethers, cyclic ethers, esters, alkanes, cycloalkanes, benzenes, amides, sulfoxides and a mixture thereof;
wherein the "acid salt" comprises an inorganic acid salt or an organic acid salt; wherein the inorganic acid salt is phosphate; and wherein the organic acid salt is selected from the group consisting of mesylate and 1,5-naphthalenedisulfonate.

6. The method according to claim 5, wherein the method is for preparing crystal form III of the mesylate salt, the method comprising:
adding methanol to the free base of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3 (4H)-one,
slowly adding an equal or excess molar equivalent of methanesulfonic acid to dissolve 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one, thereby obtaining a mixture,
immediately adding a crystal seed of crystal form III of the mesylate salt to the mixture and stirring the mixture to conduct a salt-forming reaction, and
conducting a solid-liquid separation after the salt-forming reaction is complete to obtain crystal form III of the mesylate salt;
or in the absence of a crystal seed of crystal form III of the mesylate salt,
first obtaining crystal form IV of the mesylate salt,
drying crystal form IV of the mesylate salt under vacuum at 100° C.-120° C., overnight, thereby transforming crystal form IV of the mesylate salt into crystal form III of the mesylate salt; or
dispersing crystal form V of the mesylate salt in a single or mixed anti-solvent to obtain a mixture, and
stirring the mixture at room temperature or under heating, thereby transforming crystal form V of the mesylate salt into crystal form III of the mesylate salt.

7. A pharmaceutical composition comprising a therapeutically effective amount of the crystalline acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one according to claim 1 and a pharmaceutically acceptable carrier or excipient.

8. A method for modulating a catalytic activity of a protein kinase comprising a step of contacting the protein kinase with the crystalline acid salt C according to claim 1, wherein the protein kinase is selected from the group consisting of C-Met and VEGFR receptor tyrosine kinase.

9. A method of modulating a catalytic activity of a protein kinase selected from the group consisting of C-Met and VEGFR receptor tyrosine kinase in a subject in need thereof, the method comprising administering to the subject the pharmaceutical composition of claim 7.

10. A The method of claim 9, wherein the subject is in need of treating a cancer, a hematopoietic tumor of the lymphatic system, a hematopoietic tumor of the bone marrow system, a mesenchymal tumor, a central or peripheral nervous system tumor, or other tumor, wherein the cancer is selected from the group consisting of bladder cancer, breast cancer, colon cancer, kidney cancer, liver cancer, lung cancer, stomach cancer, and skin cancer;

wherein the hematopoietic tumor of the lymphatic system is selected from the group consisting of leukemia, acute lymphocytic leukemia and chronic lymphocytic leukemia;

wherein the hematopoietic tumor of the bone marrow system is selected from the group consisting of acute or chronic myelogenous leukemia, myelodysplastic syndrome and promyelocytic leukemia;

wherein the mesenchymal tumor is selected from the group consisting of fibrosarcoma, rhabdomyosarcoma, soft tissue sarcoma and osteosarcoma;

wherein the central or peripheral nervous system tumor is selected from the group consisting of astrocytoma, neuroblastoma, glioma and nerve ending tumor; and wherein the other tumor is selected from the group consisting of malignant melanoma and Kaposi's sarcoma.

11. A method of treating a cancer, a hematopoietic tumor of the lymphatic system, a hematopoietic tumor of the bone marrow system, a mesenchymal tumor, a central or peripheral nervous system tumor, or other tumor in a subject in need thereof, the method comprising administering to the subject the pharmaceutical composition of claim 7, wherein the cancer is selected from the group consisting of bladder cancer, breast cancer, colon cancer, kidney cancer, liver cancer, lung cancer, stomach cancer, and skin cancer;

wherein the hematopoietic tumor of the lymphatic system is selected from the group consisting of leukemia, acute lymphocytic leukemia and chronic lymphocytic leukemia;

wherein the hematopoietic tumor of the bone marrow system is selected from the group consisting of acute or chronic myelogenous leukemia, myelodysplastic syndrome and promyelocytic leukemia;

wherein the mesenchymal tumor is selected from the group consisting of fibrosarcoma, rhabdomyosarcoma, soft tissue sarcoma and osteosarcoma;

wherein the central or peripheral nervous system tumor is selected from the group consisting of astrocytoma, neuroblastoma, glioma and nerve ending tumor; and wherein the other tumor is selected from the group consisting of malignant melanoma and Kaposi's sarcoma.

12. A crystalline acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3 (4H)-one, wherein the crystalline acid salt is crystal form III of a mesylate salt having an X-ray powder diffraction (XRPD) spectrum comprising peaks at diffraction angles (2θ) of 16.7±0.2°, 19.3±0.2°, 23.2±0.2°, 26.5±0.2°, 8.7±0.20, 19.5±0.2°, 21.8±0.2°, 23.6±0.2° and 24.3±0.2°.

13. The crystalline acid salt according to claim 12, wherein the XRPD spectrum further comprises peaks at diffraction angles (2θ) of 11.7±0.20, 13.6±0.2°, 14.1±0.2°, 17.2±0.20, 18.7±0.2° and 27.2±0.2°.

14. The crystalline acid salt according to claim 12, having an XRPD spectrum as shown in FIG. 17.

15. A pharmaceutical composition comprising a therapeutically effective amount of the crystalline acid salt of 9-((8-fluoro-6-(1-methyl-1H-pyrazol-4-yl)-[1,2,4]triazolo[4,3-a]pyridine-3-yl)thio)-4-methyl-2H-[1,4]oxaazido[3,2-c]quinoline-3(4H)-one according to claim 12 and a pharmaceutically acceptable carrier or excipient.

16. A method for modulating a catalytic activity of a protein kinase comprising a step of contacting the protein kinase with the crystalline acid salt according to claim 12, wherein the protein kinase is selected from the group consisting of C-Met and VEGFR receptor tyrosine kinase.

17. A method of modulating a catalytic activity of a protein kinase selected from the group consisting of C-Met and VEGFR receptor tyrosine kinase in a subject in need thereof, the method comprising administering to the subject the pharmaceutical composition of claim 15.

18. The method of claim 17, wherein the subject is in need of treating a cancer, a hematopoietic tumor of the lymphatic system, a hematopoietic tumor of the bone marrow system, a mesenchymal tumor, a central or peripheral nervous system tumor, or other tumor, wherein the cancer is selected from the group consisting of bladder cancer, breast cancer, colon cancer, kidney cancer, liver cancer, lung cancer, stomach cancer, and skin cancer;

wherein the hematopoietic tumor of the lymphatic system is selected from the group consisting of leukemia, acute lymphocytic leukemia and chronic lymphocytic leukemia;

wherein the hematopoietic tumor of the bone marrow system is selected from the group consisting of acute or chronic myelogenous leukemia, myelodysplastic syndrome and promyelocytic leukemia;

wherein the mesenchymal tumor is selected from the group consisting of fibrosarcoma, rhabdomyosarcoma, soft tissue sarcoma and osteosarcoma;

wherein the central or peripheral nervous system tumor is selected from the group consisting of astrocytoma, neuroblastoma, glioma and nerve ending tumor; and wherein the other tumor is selected from the group consisting of malignant melanoma and Kaposi's sarcoma.

19. A method of treating a cancer, a hematopoietic tumor of the lymphatic system, a hematopoietic tumor of the bone marrow system, a mesenchymal tumor, a central or peripheral nervous system tumor, or other tumor in a subject in need thereof, the method comprising administering to the subject the pharmaceutical composition of claim 15, wherein the cancer is selected from the group consisting of bladder cancer, breast cancer, colon cancer, kidney cancer, liver cancer, lung cancer, stomach cancer, and skin cancer;

wherein the hematopoietic tumor of the lymphatic system is selected from the group consisting of leukemia, acute lymphocytic leukemia and chronic lymphocytic leukemia;

wherein the hematopoietic tumor of the bone marrow system is selected from the group consisting of acute or chronic myelogenous leukemia, myelodysplastic syndrome and promyelocytic leukemia;

wherein the mesenchymal tumor is selected from the group consisting of fibrosarcoma, rhabdomyosarcoma, soft tissue sarcoma and osteosarcoma;

wherein the central or peripheral nervous system tumor is selected from the group consisting of astrocytoma, neuroblastoma, glioma and nerve ending tumor; and wherein the other tumor is selected from the group consisting of malignant melanoma and Kaposi's sarcoma.

* * * * *